United States Patent
Schrul et al.

(10) Patent No.: US 12,377,220 B2
(45) Date of Patent: Aug. 5, 2025

(54) ASSEMBLY FOR AN INJECTION OR INFUSTION DEVICE

(71) Applicant: Ypsomed AG, Burgdorf (CH)

(72) Inventors: Christian Schrul, Burgdorf (CH); Stefan Burren, Schwarzenburg (CH); Mario Bernhard, Burgdorf (CH); Bernhard Bigler, Niederönz (CH); Simon Scheurer, Bern (CH)

(73) Assignee: Ypsomed AG, Burgdorf (CH)

( * ) Notice: Subject to any disclaimer, the term of this patent is extended or adjusted under 35 U.S.C. 154(b) by 1101 days.

(21) Appl. No.: 17/017,182

(22) Filed: Sep. 10, 2020

(65) Prior Publication Data

US 2021/0001048 A1    Jan. 7, 2021

Related U.S. Application Data

(63) Continuation of application No. PCT/IB2019/051357, filed on Feb. 20, 2019.

(30) Foreign Application Priority Data

Mar. 15, 2018    (EP) .................................... 18161873

(51) Int. Cl.
*A61M 5/24* (2006.01)
*A61M 5/142* (2006.01)

(52) U.S. Cl.
CPC ...... *A61M 5/2466* (2013.01); *A61M 5/14248* (2013.01); *A61M 2005/247* (2013.01); *A61M 2207/00* (2013.01)

(58) Field of Classification Search
CPC ........ A61M 5/2466; A61M 2025/0035; A61M 2005/247; A61M 2039/0686;

(Continued)

(56) References Cited

U.S. PATENT DOCUMENTS

| 3,260,147 A | 7/1966 | Farabee |
| 3,260,149 A | 7/1966 | Deaver |

(Continued)

FOREIGN PATENT DOCUMENTS

| EP | 2512552 B1 | 2/2015 |
| EP | 3260147 A1 | 12/2017 |

(Continued)

OTHER PUBLICATIONS

International Preliminary Report on Patentability received for International Application No. PCT/IB2019/051357, mailed on Sep. 15, 2020.

(Continued)

*Primary Examiner* — James D Ponton
(74) *Attorney, Agent, or Firm* — Dorsey & Whitney LLP

(57) ABSTRACT

An assembly for an injection or infusion device includes i) a cartridge being closed by a septum and the surface of the septum being sterile and covered by a first continuous flexible strip, and ii) a fluid path unit comprising a cartridge holder and a fluid path compartment comprising a needle in an interior, the needle is configured to penetrate the septum of the cartridge through a passage in the fluid path compartment. The passage is closed by a second continuous flexible strip keeping the interior of the fluid path compartment in a sterile condition. The cartridge is inserted into the cartridge holder aligning the septum with the passage and sandwiching both strips between the septum and the fluid path compartment. Both strips may be simultaneously removable from the cartridge and fluid path compartment thereby, establishing a sterile connection between the septum and the interior of the fluid path compartment.

20 Claims, 17 Drawing Sheets

(58) Field of Classification Search
CPC .......... A61M 5/285; A61M 2005/2492; A61M 5/2455; A61M 5/2459; A61M 5/162; A61M 5/14566; A61M 2039/1072; A61M 39/165; A61M 39/18; A61M 39/20; A61M 39/14; A61M 2005/312; A61M 2205/0205; A61M 2005/3118; A61M 2005/3117; A61M 2005/3103; A61M 2005/287; A61M 5/14248; A61M 2207/00; A61M 2005/2407; A61M 2005/3121; A61M 5/3134; A61M 5/3204; A61J 1/1406; A61J 1/2024; A61J 1/202
USPC ........................................................ 604/151
See application file for complete search history.

(56) References Cited

U.S. PATENT DOCUMENTS

| | | | |
|---|---|---|---|
| 3,260,151 | A | 7/1966 | Jones |
| 3,909,910 | A | 10/1975 | Rowe et al. |
| 4,019,512 | A | 4/1977 | Tenczar |
| 5,019,047 | A | 5/1991 | Kriesel |
| 6,382,442 | B1 | 5/2002 | Thibault et al. |
| 6,679,529 | B2 | 1/2004 | Johnson et al. |
| 6,843,782 | B2 | 1/2005 | Gross et al. |
| 8,315,687 | B2 | 11/2012 | Cross et al. |
| 9,248,232 | B2 | 2/2016 | Yodfat et al. |
| 9,427,529 | B2 | 8/2016 | Cabiri |
| 10,758,721 | B2 | 9/2020 | Sonderegger et al. |
| 2001/0056262 | A1 | 12/2001 | Cabiri et al. |
| 2003/0030272 | A1* | 2/2003 | Johnson ............... F16L 29/00 285/70 |
| 2004/0116866 | A1 | 6/2004 | Gorman et al. |
| 2008/0048436 | A1 | 2/2008 | Matkovich et al. |
| 2009/0095290 | A1* | 4/2009 | Cain .................... A61L 2/206 128/202.22 |
| 2011/0166512 | A1 | 7/2011 | Both et al. |
| 2012/0316506 | A1 | 12/2012 | Sonderegger et al. |
| 2014/0008366 | A1 | 1/2014 | Genosar |
| 2015/0061282 | A1* | 3/2015 | Faldt .................... A61M 39/16 285/124.5 |
| 2015/0105691 | A1 | 4/2015 | Hadvary et al. |
| 2015/0217058 | A1* | 8/2015 | Hooven ................ A61M 5/145 604/403 |
| 2015/0320990 | A1 | 11/2015 | Burton et al. |
| 2016/0089056 | A1 | 3/2016 | Limaye et al. |
| 2016/0199568 | A1* | 7/2016 | McNall, III ...... A61M 5/14232 53/425 |
| 2016/0220798 | A1 | 8/2016 | Netzel et al. |
| 2016/0256665 | A1* | 9/2016 | Doshi ....................... A61F 5/08 |
| 2016/0310663 | A1 | 10/2016 | Dantsker |
| 2016/0310665 | A1 | 10/2016 | Hwang et al. |
| 2017/0020423 | A1 | 1/2017 | Fujita et al. |
| 2017/0259015 | A1 | 9/2017 | Caspers |
| 2018/0353704 | A1 | 12/2018 | Helmer |
| 2019/0240417 | A1 | 8/2019 | Hostettler et al. |
| 2019/0274924 | A1 | 9/2019 | Barmaimon et al. |
| 2019/0374707 | A1 | 12/2019 | Damestani et al. |
| 2020/0001068 | A1 | 1/2020 | Donze et al. |
| 2020/0297917 | A1 | 9/2020 | Helmer et al. |
| 2020/0316290 | A1 | 10/2020 | Bourelle et al. |
| 2020/0397984 | A1 | 12/2020 | Reed et al. |
| 2020/0405950 | A1 | 12/2020 | Burren et al. |
| 2020/0405951 | A1 | 12/2020 | Burren et al. |
| 2020/0405952 | A1 | 12/2020 | Rytz et al. |
| 2021/0030949 | A1 | 2/2021 | Damiano et al. |
| 2021/0038805 | A1 | 2/2021 | Goldstein |
| 2021/0093849 | A1 | 4/2021 | Stumpe et al. |
| 2021/0128844 | A1 | 5/2021 | Boyaval et al. |
| 2021/0170095 | A1 | 6/2021 | Diperna et al. |
| 2021/0260279 | A1 | 8/2021 | Boyaval et al. |

FOREIGN PATENT DOCUMENTS

| | | | |
|---|---|---|---|
| EP | 3260149 | A1 | 12/2017 |
| EP | 3260151 | A1 | 12/2017 |
| EP | 3052166 | B1 | 4/2019 |
| EP | 3539591 | A1 | 9/2019 |
| EP | 3539592 | A1 | 9/2019 |
| EP | 3539596 | A1 | 9/2019 |
| EP | 3545997 | A1 | 10/2019 |
| EP | 3582825 | A1 | 12/2019 |
| EP | 3697475 | A1 | 8/2020 |
| WO | 9959665 | A1 | 11/1999 |
| WO | 2006067217 | A2 | 6/2006 |
| WO | 2008068695 | A1 | 6/2008 |
| WO | 2011015659 | A1 | 2/2011 |
| WO | 2011064780 | A2 | 6/2011 |
| WO | 2011075099 | A1 | 6/2011 |
| WO | 2017089271 | A1 | 6/2017 |
| WO | WO-2017089286 | A1 * | 6/2017 ............ A61M 39/04 |
| WO | 2017219155 | A1 | 12/2017 |
| WO | 2018151890 | A1 | 8/2018 |
| WO | 2019175688 | A1 | 9/2019 |
| WO | 2019175689 | A1 | 9/2019 |
| WO | 2019175690 | A1 | 9/2019 |
| WO | 2019186375 | A1 | 10/2019 |

OTHER PUBLICATIONS

International Preliminary Report on Patentability received for International Application No. PCT/IB2019/051358, mailed on Sep. 15, 2020.
International Preliminary Report on Patentability received for International Application No. PCT/IB2019/051359, mailed on Sep. 15, 2020.
International Preliminary Report on Patentability Received for International Application No. PCT/IB2019/052421, mailed on Sep. 29, 2020, 6 pages.
Extended European Search Report received for European patent application No. 18164145.7, issued on Nov. 12, 2018, 6 page.
International Search Report and Written Opinion received for International Application No. PCT/IB2019/051357 mailed on May 7, 2019, 12 pages.
International Search Report and Written Opinion received for International Application No. PCT/IB2019/051358, mailed on May 15, 2019, 9 pages.
International Search Report and Written Opinion received for International Application No. PCT/IB2019/051359, mailed on May 15, 2019, 10 pages.
International Search Report and Written Opinion received for International Application No. PCT/IB2019/052421, mailed on Aug. 6, 2019, 10 pages.

* cited by examiner

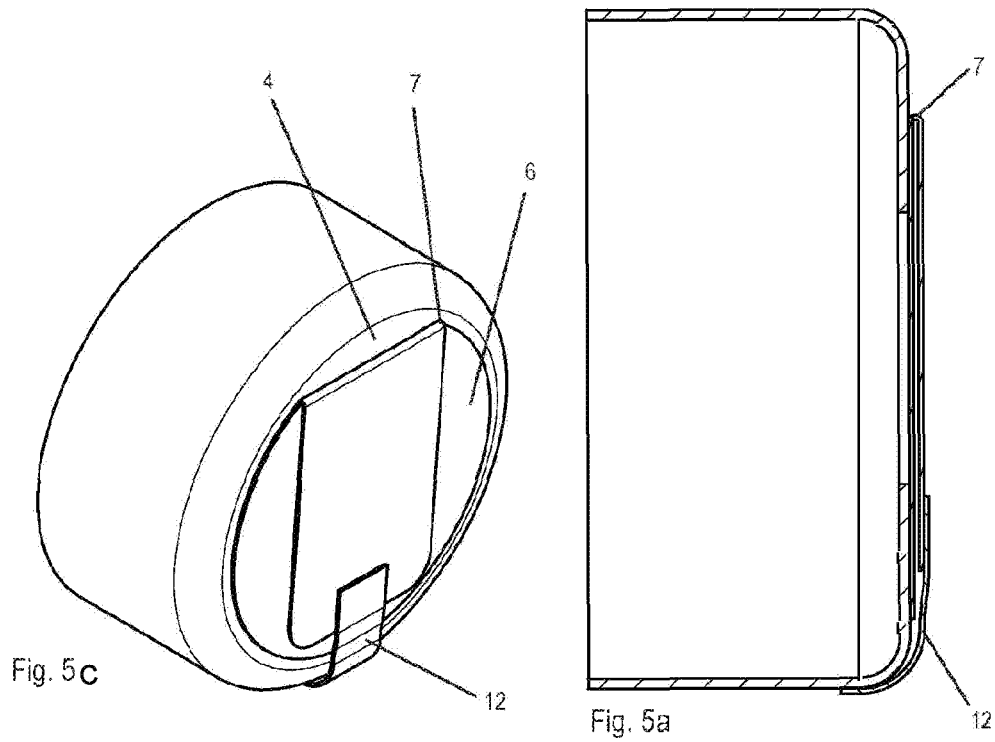
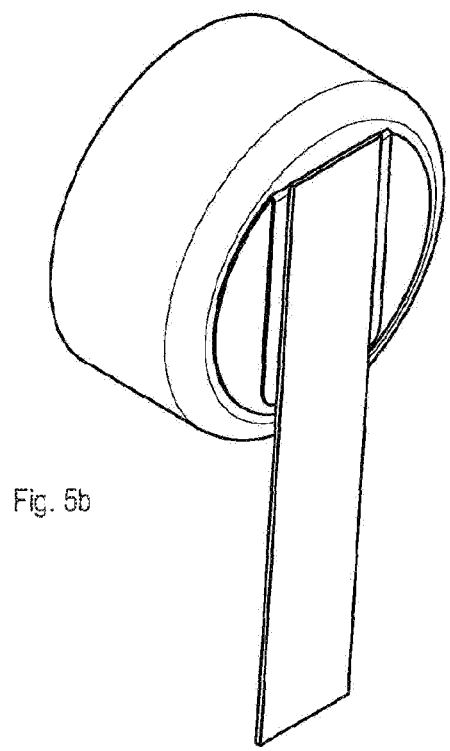

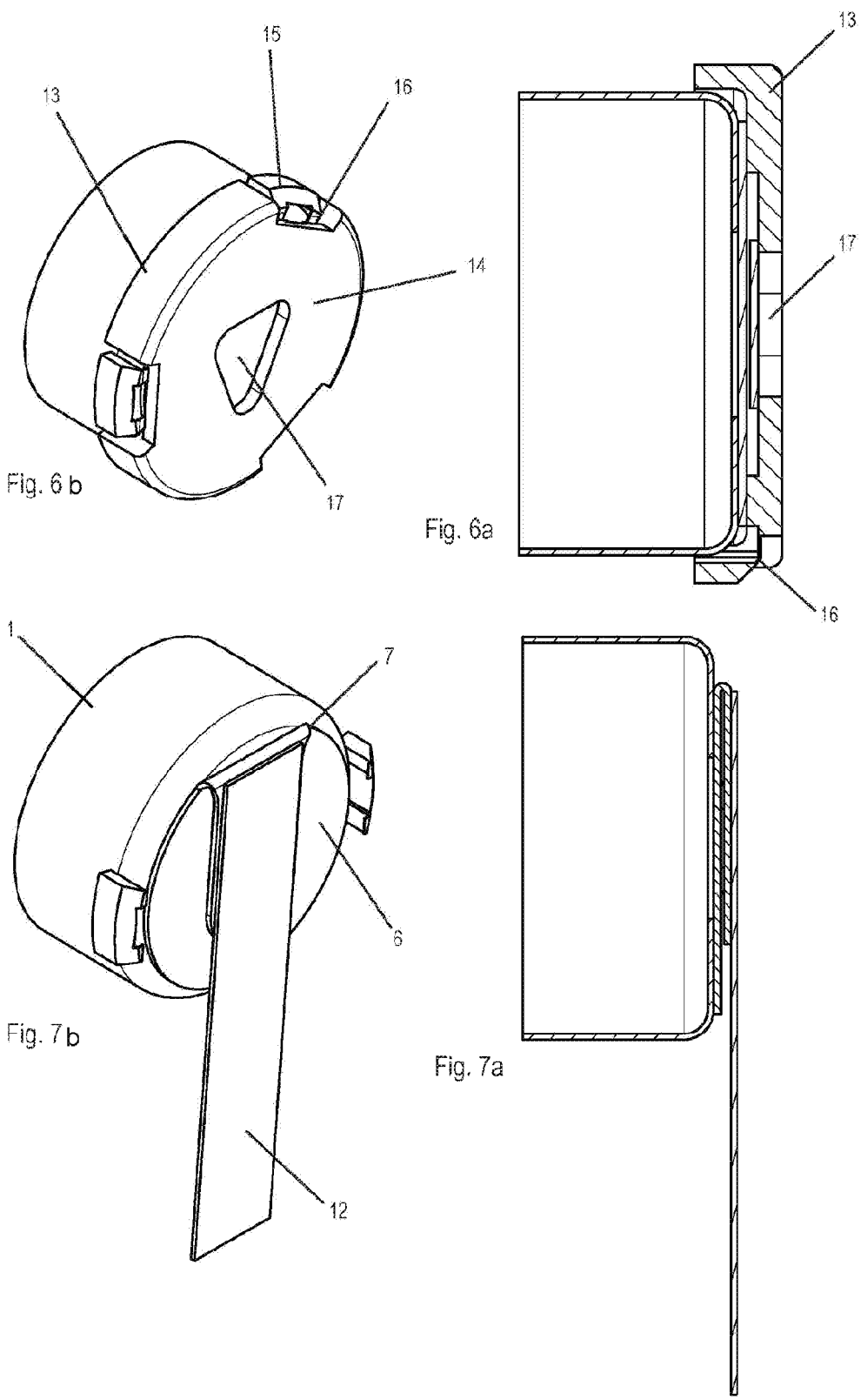

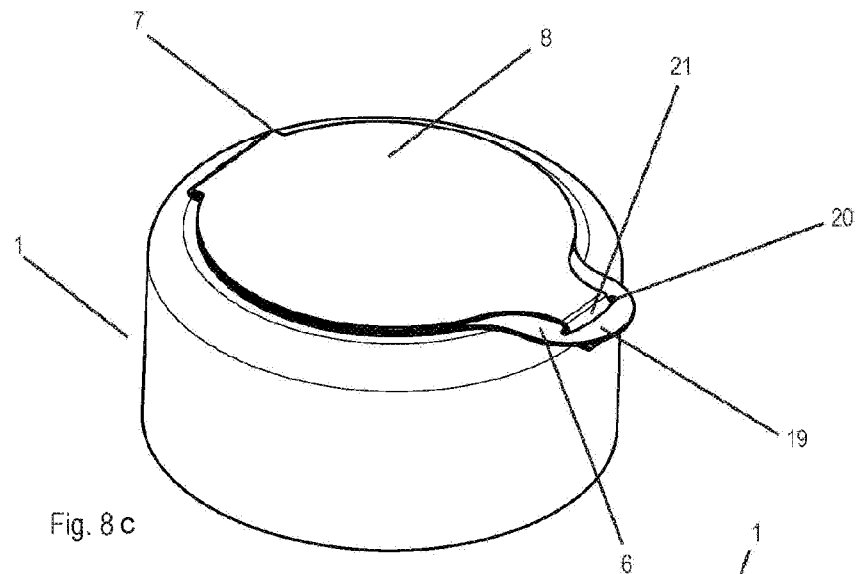
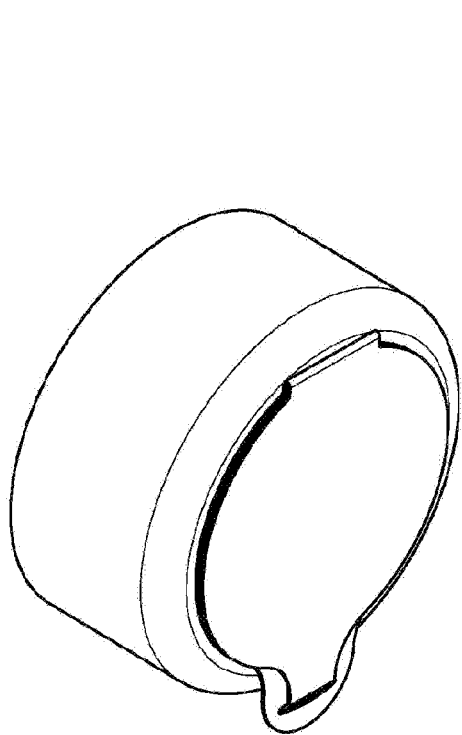
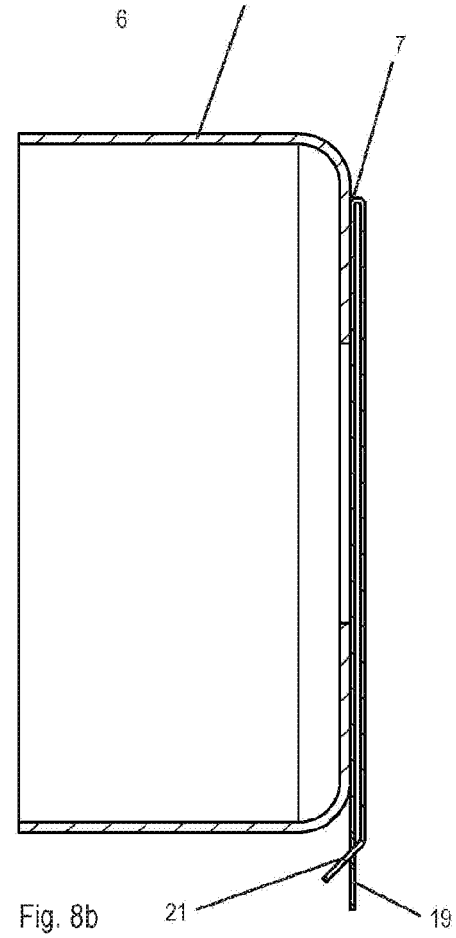
Fig. 8c
Fig. 8a
Fig. 8b

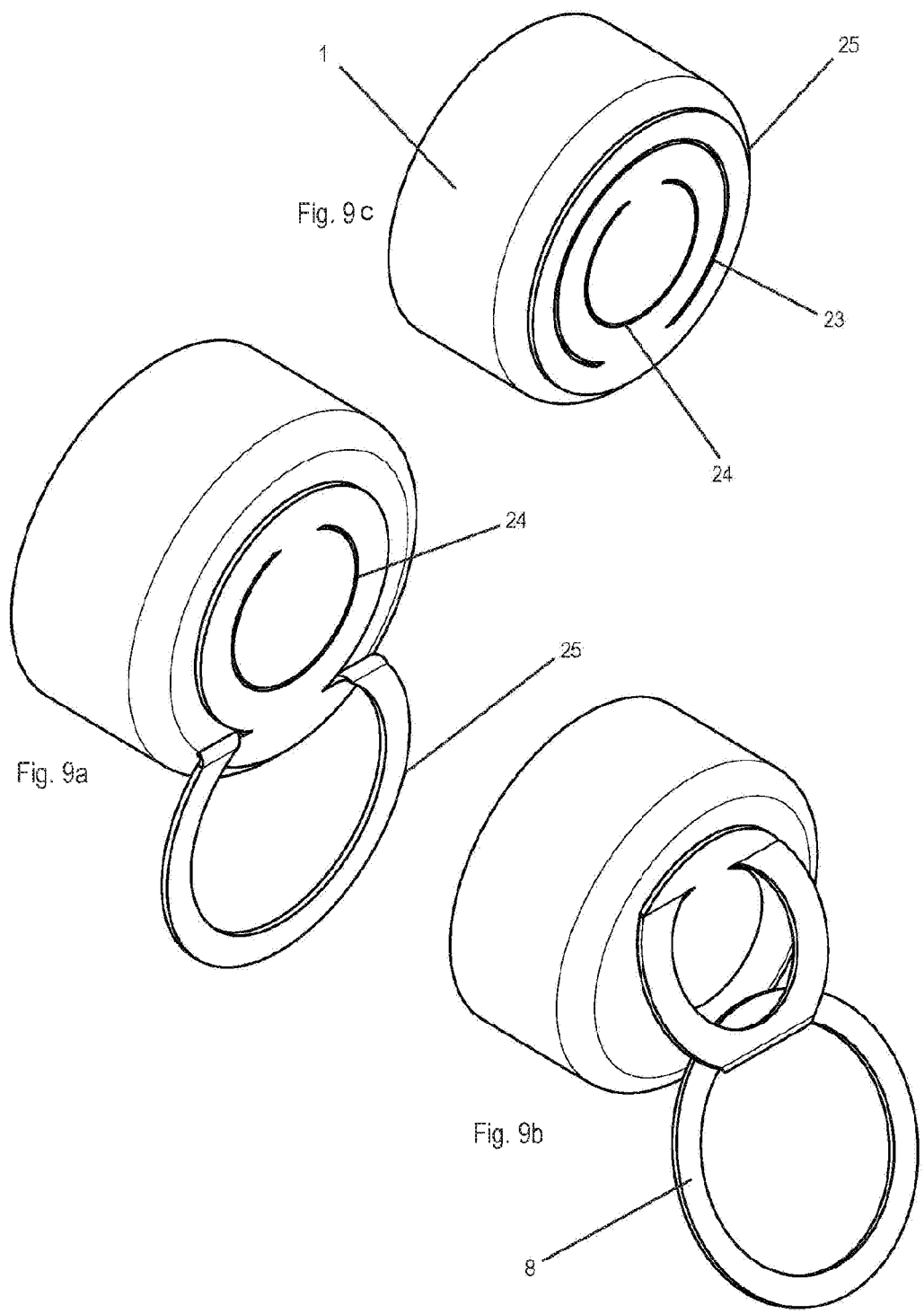

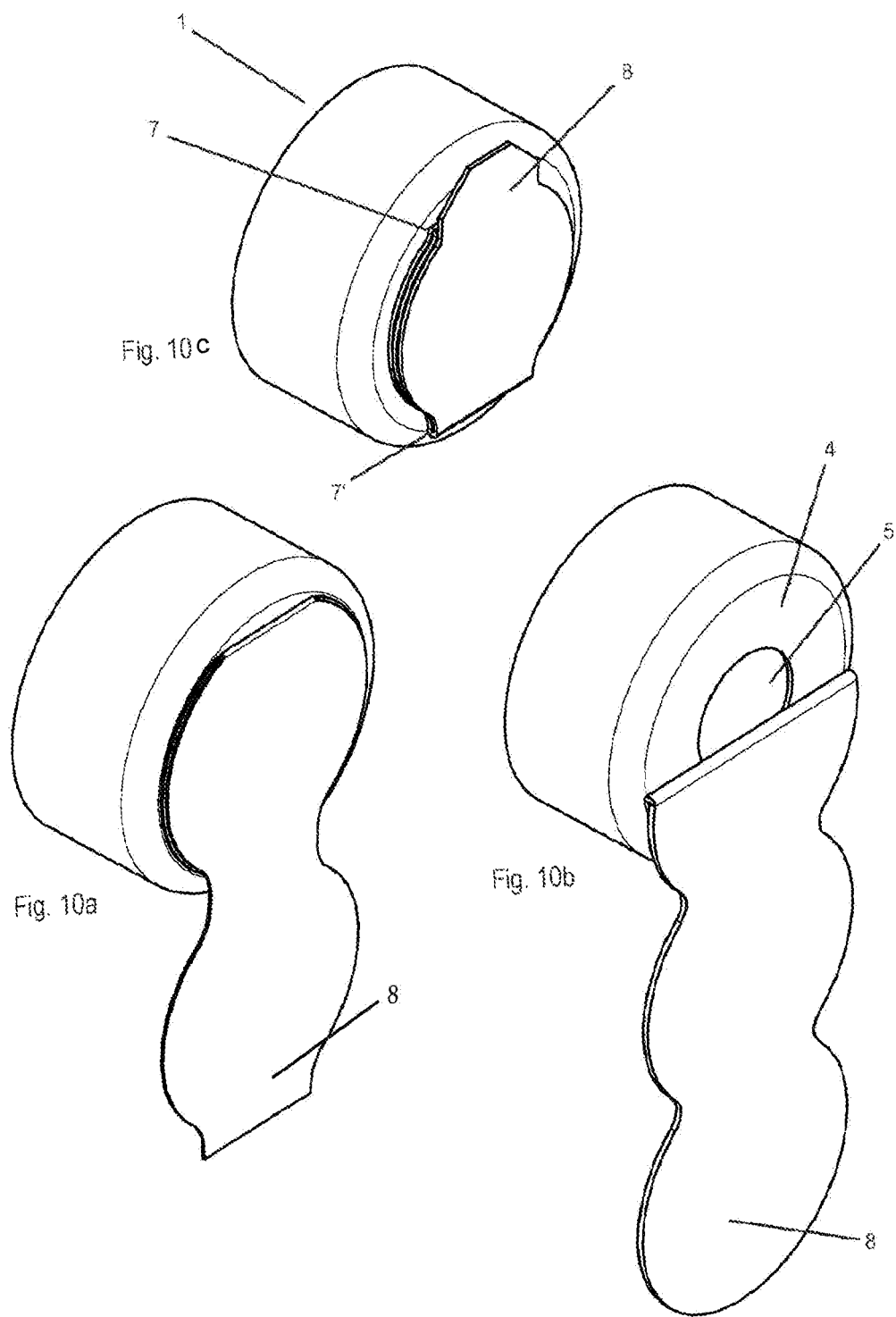

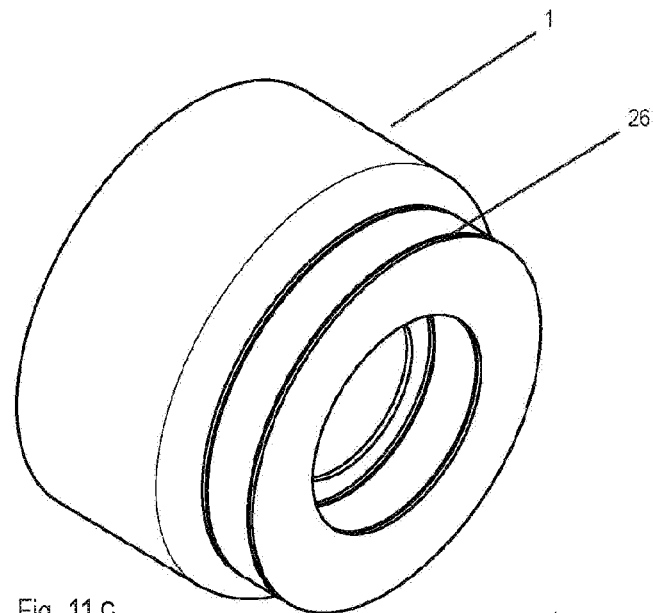
Fig. 11c
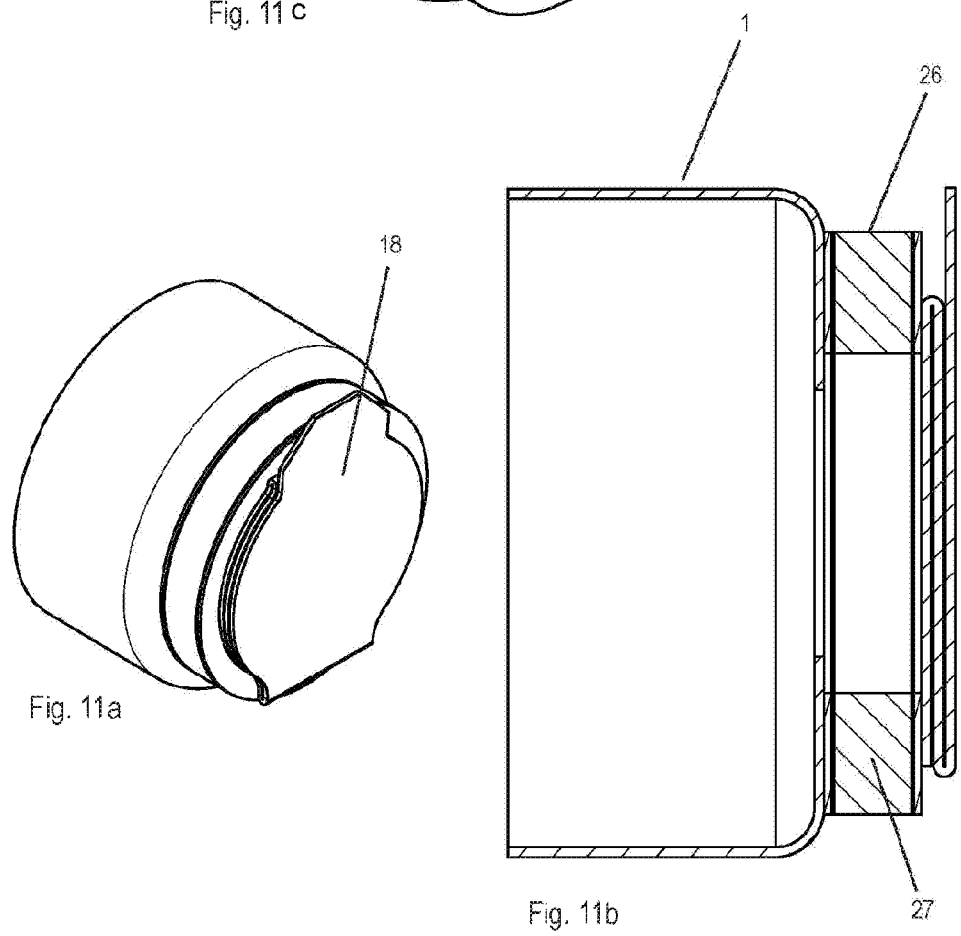
Fig. 11a
Fig. 11b

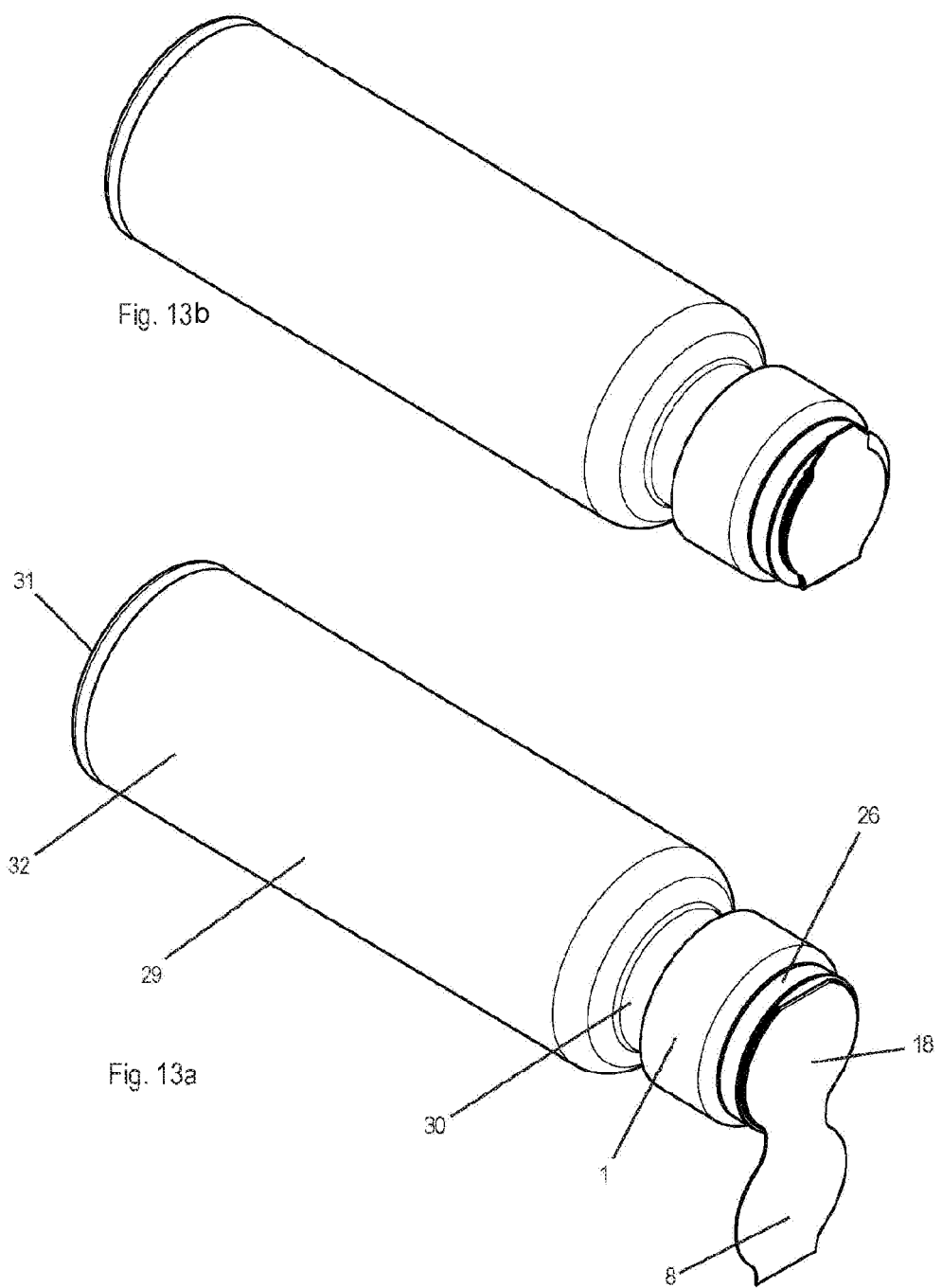

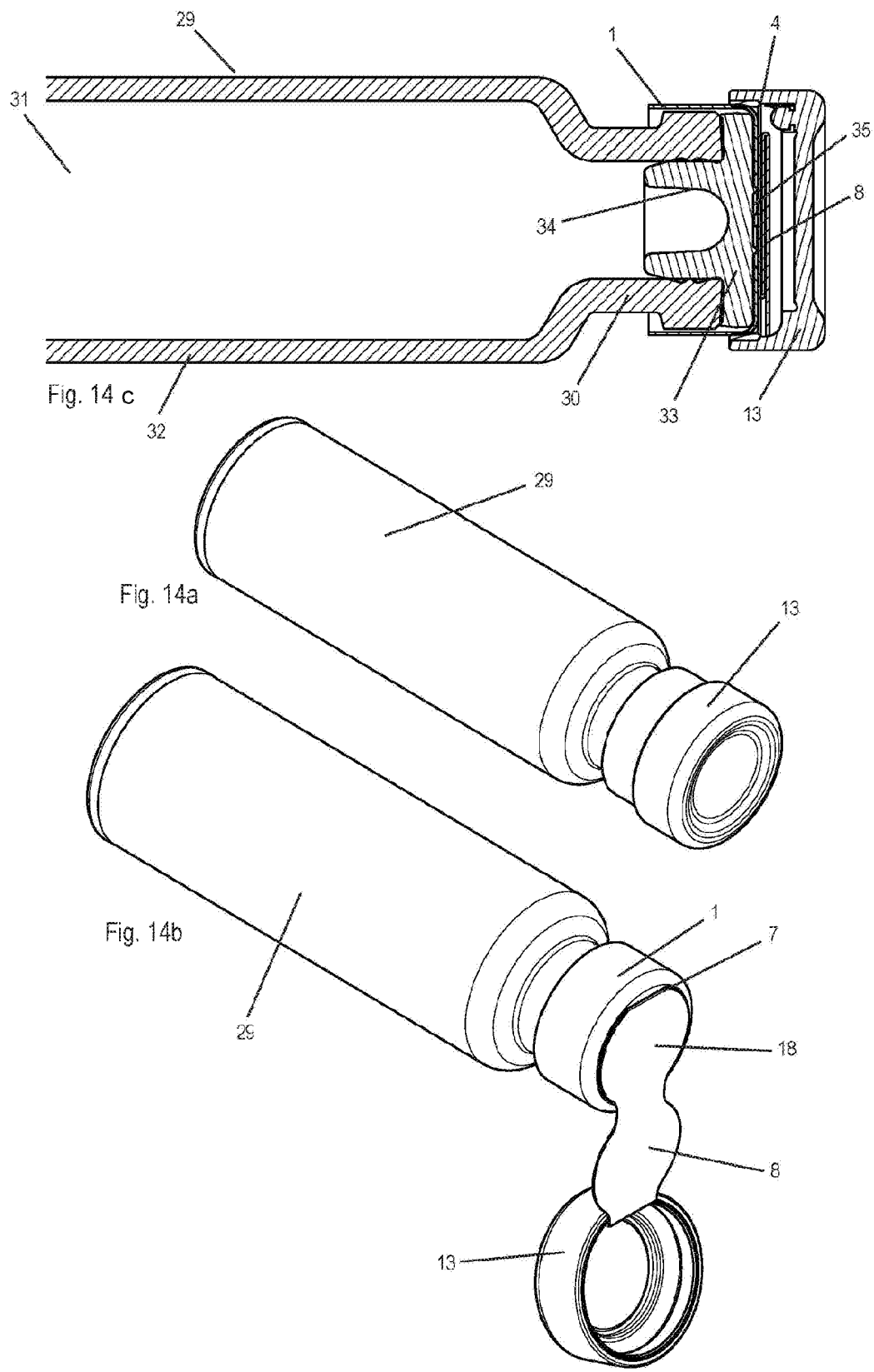

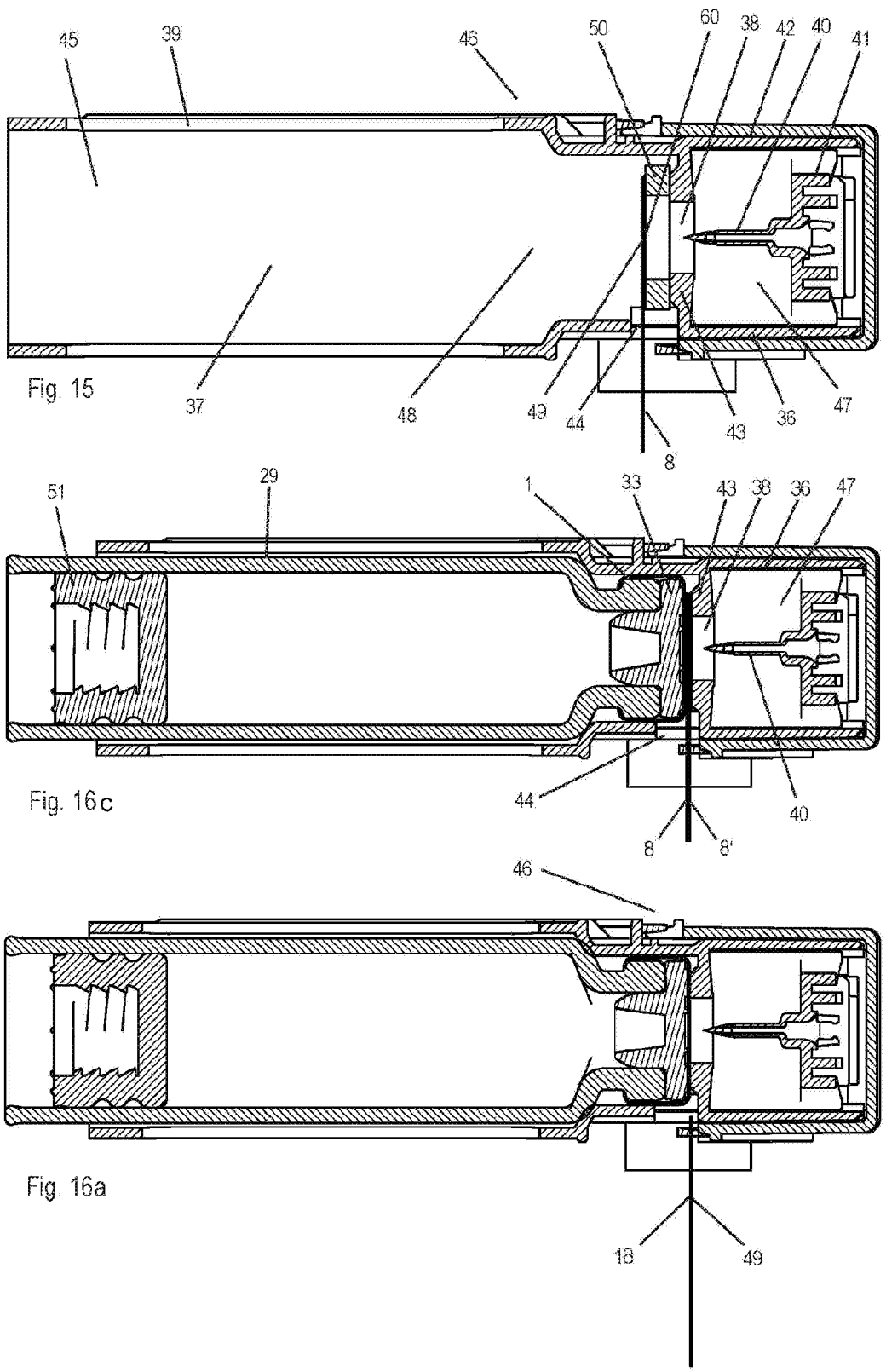

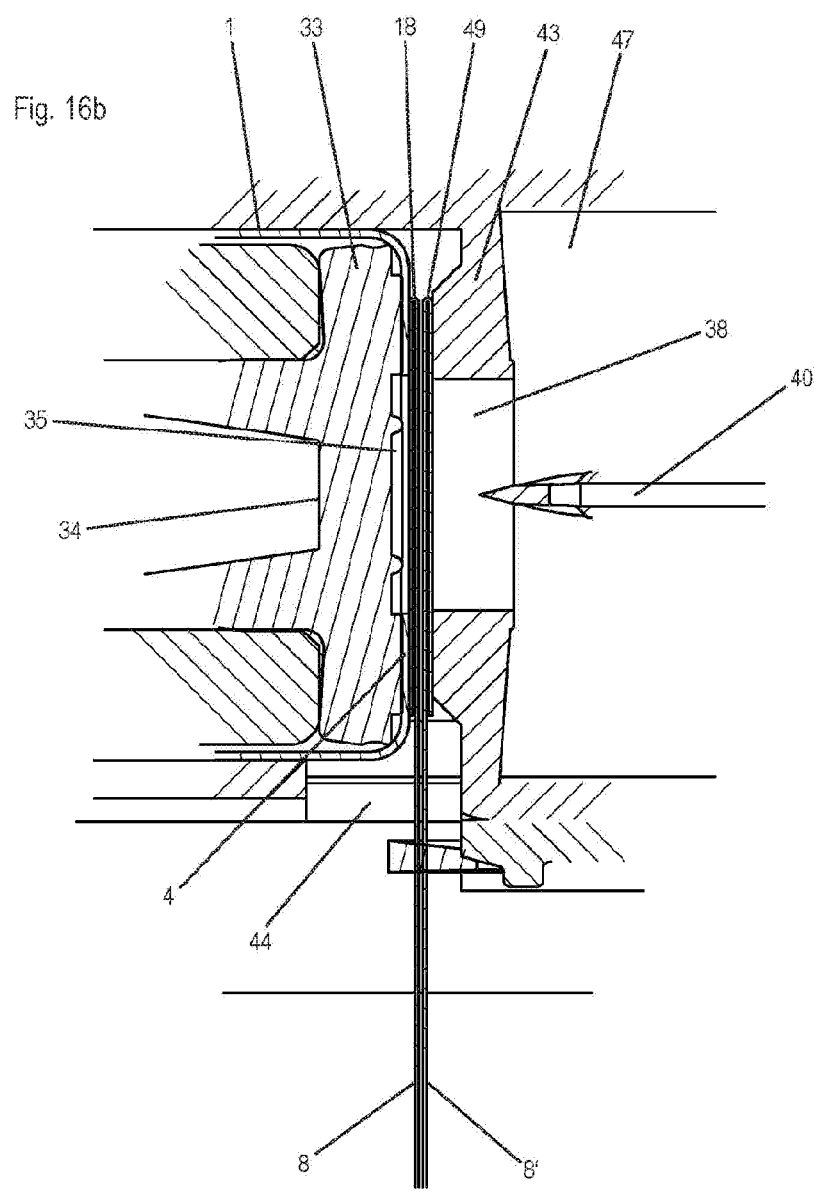

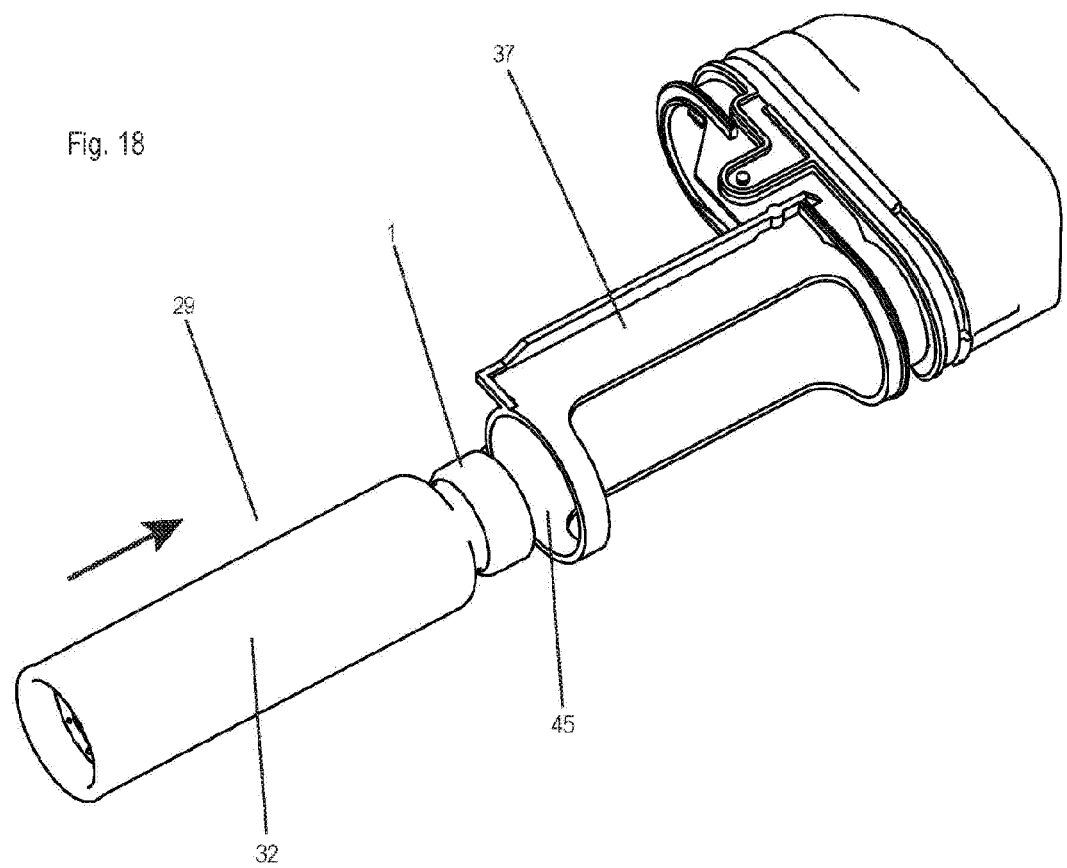

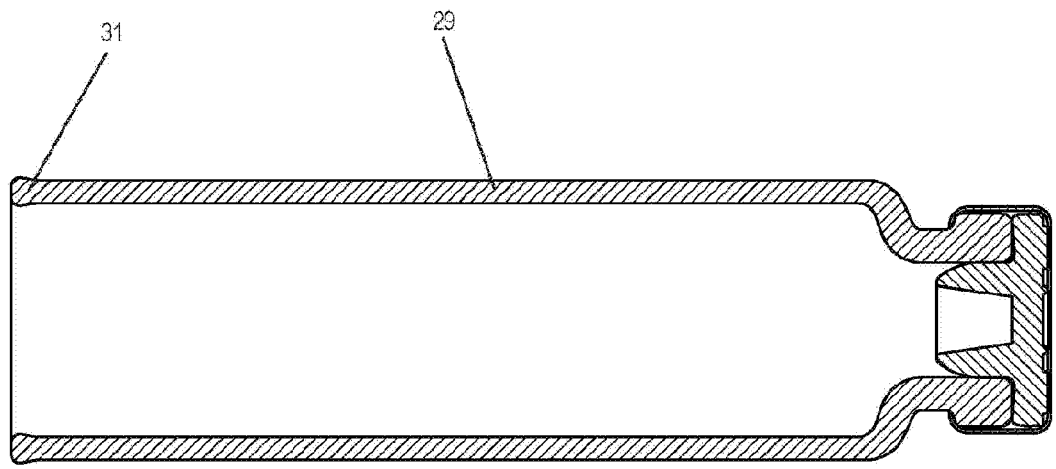
Fig. 19
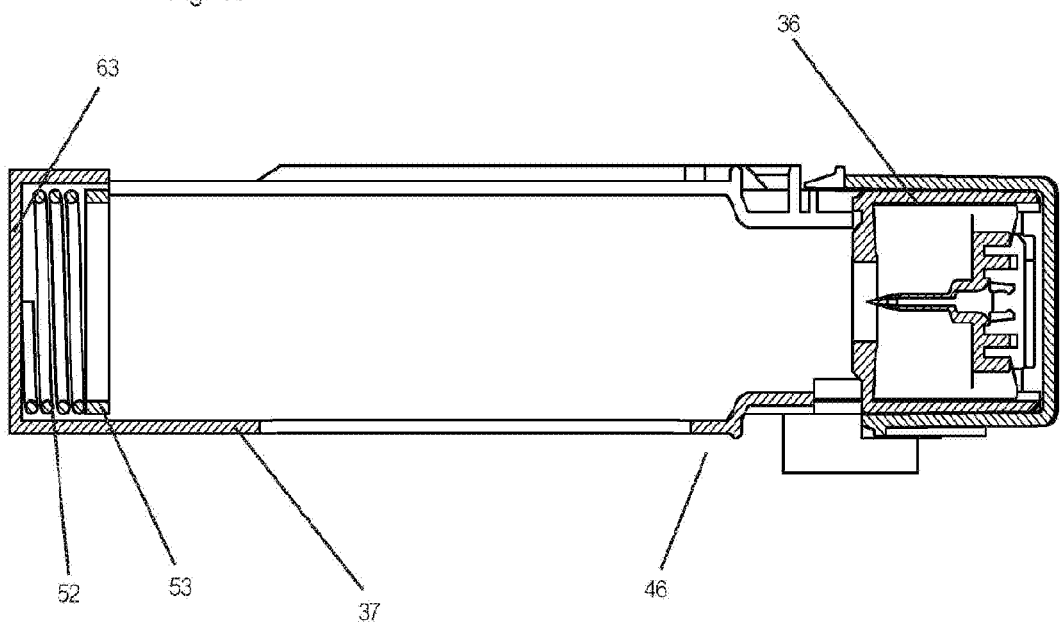

ASSEMBLY FOR AN INJECTION OR INFUSION DEVICE

CROSS-REFERENCE TO RELATED APPLICATIONS

This application is a continuation of International Patent Application No. PCT/IB2019/051357, filed Feb. 20, 2019, entitled "AN ASSEMBLY FOR AN INJECTION OR INFUSION DEVICE," which claims priority of European Patent Application No. 18161873.7, filed Mar. 15, 2018, entitled "AN ASSEMBLY FOR AN INJECTION OR INFUSION DEVICE", each of which is incorporated by reference herein, in their entireties and for all purposes.

TECHNICAL FIELD

Assemblies for an injection or infusion devices are configured for delivery of a medicament to a patient. More particularly, the assemblies comprise at least one continuous flexible strip removable therefrom for establishing a sterile connection between opposing surfaces.

BACKGROUND

Injection and infusion devices are used for the subcutaneous delivery of liquid medicaments to a patient. Such injection devices are often pen-shaped, having a long axis and are called injection pens. The injection pens comprise a housing, which can hold a dose setting and dose delivery mechanism. The medication is preferably present in a cartridge or in a prefilled syringe. A cartridge is normally attached to the housing of the injection pen using a cartridge holder. The user sets a dose of medication which is subsequently delivered from the cartridge. Such injection pens are used to deliver separate injections and not intended for continuous delivery of a medicament. A needle is attached to the injection pen each time before use and the needle penetrates a septum present on the cartridge.

Infusion devices deliver the medication from the cartridge using a drive mechanism and a control mechanism that controls the advancement of a plunger present in the cartridge containing the medication. The medication is delivered to the patient via fluid path and an external infusion set comprising a needle for subcutaneous delivery. With such infusion devices both continuous and temporary profiles can be programmed for delivery to the patient.

A patch device is an example of an infusion device that is attachable to the skin of the patient. Such patch devices do not need an external infusion set for delivery as the needle is directly contained in the patch device and inserted into the patient therefrom.

The injection and infusion devices comprise a dose setting mechanism, a delivery mechanism, a needle insertion and retraction mechanism or a needle shield protection system which is connected or connectable to a drive mechanism. The drive mechanism is fueled by a power source which supplies energy to the injection or infusion device for executing tasks such as medication delivery, establishing a connection between the fluid path and the cartridge, needle insertion, needle retraction, advancing and/or retracting a piston rod, signaling to the user that the medication is complete, signaling to the user that the device can be removed, powering a processor unit in the device or establishing a wireless connection for data transmission to an external such as a smart phone. The power source used in such injection or infusion devices can be selected from a wide variety of options such as, but not limiting to, a spring (compression, torsional spring, and leaf spring), an electromotor, a battery, pressurized gas or liquid-hydraulic systems and the like. In the injection and infusion devices, several operations need to be arranged in a certain sequence for a correct operation and transmission of power from the energy source to final medicament delivery, for example, by advancing a plug in a cartridge.

For example for a patch infusion device, the needle must be inserted first, either using a steel needle (cannula) or a combination of a steel needle with a soft cannula; subsequently the steel needle must be retracted to leave the soft cannula in the subcutaneous tissue of the patient, followed by delivery of medication. Preferably, the needle, either soft of steel is retracted into the device before the patch device can be removed from the body. Alternatively, the needle is not retracted but a needle shield is extended from the body of the device to protect the needle tip and prevent needle sticks of the patient.

The term "medicament" or "medication" includes any flowable medical formulation suitable for controlled administration through a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The liquid medicament is produced under sterile conditions and enclosed in a container to keep the medicament sterile. Such a container can be a cartridge or an ampoule, both of which are preferably made of glass or plastic. As an alternative plastic containers may be used. A cartridge comprises a barrel having two openings, one opening at the end of a neck portion and a second opening opposite to the neck portion. The opening at the neck portion is normally closed by a penetrable septum that is attached to the neck portion using a crimp. The opposite opening is closed by a plug and the medicament is enclosed by the barrel between the septum and the plug. During medication delivery, the plug in the cartridge is advanced in the cartridge by the drive mechanism. The cartridge is filled with the liquid medicament in a fill finish line, and either the plug is inserted first into the barrel and the medicament is filled via the neck portion followed by closure using the septum, or the septum is attached first to the cartridge and the medicament is filled from the opposite opening and finally closed by the plug. The fill finish is done in a sterile environment. The filled cartridge is normally subjected to a visual inspection to ensure that no particulates are present in the liquid.

The filled cartridge is assembled with an injection or infusion device, preferably a patch device, having a fluid path unit that is used for establishing the connection between a fluid path and the liquid medicament. The fluid path unit comprises a compartment or containment for housing a fluid path in the interior. The fluid path may comprise a needle or spike that can pierce through the septum of the cartridge, a tubing for fluid transfer connecting the needle or spike to a second needle intended for penetrating the skin of the patient. During storage (e.g., prior to use) there is no connection between the cartridge and the fluid path unit, and just prior to use the connection may be established. The interior of the compartment or containment for the fluid path unit is sterilized during manufacturing and remains in a sterile condition during storage. The assembly of the fluid path unit with the compartment or containment and the cartridge can occur in a sterile environment which may be cumbersome (for example in view of the visual inspection) and expensive, or it is assembled in a non-sterile environment such as a clean room. The device comprising the assembly of the fluid path and cartridge can be in a sterile packaging during storage, which is removed just before use, or is in a non-sterile packaging. In either option, a sterile connection needs to be established between the content of the cartridge and the fluid path in the compartment or containment of the fluid path unit prior to use, and this is usually done in a non-sterile environment.

US20160199568 discloses an infusion device with a peristaltic pump. The tubing of the pump is connected to a connector assembly comprising an ampoule with a liquid medicament and a connector for the tubing. Between the ampoule and the connector there are two strips to prevent the liquid passing from the ampoule to the tubing. The ampoule is directly closed by the film and not with a septum, and the connector for the tubing is always connected to the ampoule—there is no spike or needle for establishing the connection between the liquid medicament just prior to use. Removing the strip simultaneously establishes: a) a fluid connection between the cartridge and the tubing, and b) a sterile connection between the ampoule and the tubing. The fact that there is no separate closure for the ampoule reduces the reliability of the fixed connection and cannot be used for a modular assembly approach; moreover it will be cumbersome to use standard fill-finish procedures and standard components (such as a cartridge closed by a septum) for the device described in US20160199568.

In U.S. Pat. No. 4,019,512, a sterile connection between two connector ends of two tubes is established in a non-sterile environment by removing two strips from the two connector ends. The two strips keep the ends of the tubes in a sterile environment during storage and prior to use and the strips are removed after the two connector ends have been connected. The sterile connection established is for two tubes and is not intended or suitable for establishing a connection between a cartridge and a fluid path unit of an infusion device.

The current application differs from US20160199568 in that a cartridge is provided that is closed with a septum and therefore steps a) and b) that are mentioned above and occur simultaneously in the prior art are separated from each other. First a sterile connection is established between the fluid path and the standard cartridge, and secondly, the spike or needle of the fluid path penetrates the septum of the cartridge to establish the fluid connection. The advantage of having a standard cartridge closed by a septum and crimp is that standard production procedures can be used for fill-finish of the cartridge using standard components, which increases the reliability of the assembly and the acceptance by pharmaceutical companies. A modular approach can be used, the cartridge may be filled at a different location then the assembly with the fluid path unit. Another advantage is that the cartridge with the sterile surface on the septum can be assembled with the sterile fluid path unit in a non-sterile environment. The connection shown in US20160199568 must be assembled in a sterile environment.

It is an object of the present invention to overcome the above mentioned drawbacks for an assembly between a cartridge and a fluid path unit where a reliable connection and sterile connection between the cartridge and the fluid path can be established just prior to use. It is a further object that the assembly is configured to facilitate the assembly of the device in a non-sterile environment and still enables a sterile connection between the fluid path and the cartridge upon use; both parts of the assembly can be separately assembled and sterilized before forming the assembly between the cartridge and the fluid path unit.

These objects are solved by the current invention by applying a septum to the cartridge which can be penetrated with a needle just prior to use, e.g., during storage, there is no connection at all between the fluid path and the cartridge. The cartridge with the septum is covered by a protective flexible strip that keeps the surface of the septum in a sterile condition even if the cartridge is in a non-sterile environment. The fluid path with a needle is in the interior of a compartment or containment, which is sterile and which has a passage where the needle of the fluid path can pass to penetrate the septum during use. Prior to use the passage is covered by a second protective flexible strip that keeps the interior in a sterile condition during storage. Both strips ensure that the stability of the sterile environment during storage is guaranteed and that a sterile connection can be established just prior to using the device by simultaneously removing both strips.

SUMMARY

In the present disclosure, presented are: a cartridge for use in an assembly, a crimp for the cartridge, an assembly comprising a fluid path unit and a cartridge, and a method for assembling the assembly.

The cartridge comprises a barrel having two open ends, one of which is closed by a septum with a crimp. The crimp has an end wall with a center hole and the crimp fastens the septum to a shoulder section of the barrel. The end wall of the crimp partially covers the septum, whereas the center hole allows for a needle (steel or plastic) to move through the center hole of the crimp and penetrate the septum. The septum is protected by a barrier film (for sterility) that covers the center hole and the barrier film allows for sterilization gases to pass through the film to sterilize the surface of the septum closest to the barrier film. The barrier film may be attached to the end wall of the crimp. The barrier film thus allows for sterilization of the septum and thereafter forms a sterile barrier in that the septum's surface remains sterile. The barrier film may have one or more areas covering the center hole of the crimp and a free end connected thereto. The barrier film may be shaped as a strip made from a flexible material having an area covering the septum and a free end connected thereto. The flexible strip may be folded, for example, and may comprise a plurality of U-shaped folds or may comprise cut-outs, and passages such that the folded flexible strip remains in the folded configuration. Additionally, an adhesive, heat sealing, glue or additional adhesive tape may stabilize the folded configuration. The barrier film may be protected by a cap, which covers the barrier film.

The barrier film for sterility may be a film that can be penetrated by gasses or fluids. An example of such a film is a porous membrane such as Tyvek® (polyethylene based) or GoreTex® (fluoropolymer based porous membrane). The barrier film for sterility may also be a barrier film for gases as well, an example of such a film is a non-porous membrane made of polyester and/or polyamide. The gas barrier properties may be enhanced by coating the film with a metal layer (aluminum for example) or by a layer of glass (SiOx). Such films may be single layered or multilayered comprising alternating layers of a different composition.

A crimp comprising a cylindrical section may be plastically deformed and may comprise an end wall having a center hole. The crimp may be made of aluminum. The barrier film or strip is attached to the end-wall of the crimp. The barrier film or strip is removably attached to the end-wall of the crimp, thus the strength of the adhesive connection between the crimp and the film is below the tear strength of the film. The film may be made from a flexible material such that it can be bent or folded without damaging the film. The film covers the hole and at least partially the end wall. The part of the film covering the hole may have a convex or concave shape. The additional film material in the convex or concave part may compensate for dimensional changes during the production process, for example during a sterilization step, and thus prevent tension on the connection between the end-wall of the crimp and the film.

A crimp is provided for fixating and holding a septum to a cartridge, and the crimp may comprise an open cylindrical section made from a material that can be plastically deformed and the cylindrical section may be closed by an end wall having a passage. The end wall may be arranged substantially perpendicular to an axis of the cylindrical section. The passage may be arranged such that an external needle or spike may penetrate the septum via the passage. The crimp may further comprise a strip that is attached to the end wall and which closes the passage, and the strip may be made from a flexible membrane. The strip is attached and arranged with respect to the end wall of the crimp such that the section of the strip covering the passage has a convex or concave shape, thus the lateral dimensions of the part of the strip closing the passage exceed the dimensions of the passage.

An assembly for an injection or infusion device is presented wherein the injection or infusion device may be a patch injector, a patch pump or an autoinjector having a medicament cartridge with a septum. The assembly comprises a cartridge comprising a sterile liquid medicament contained in a barrel or cartridge and being closed by a septum fastened to the barrel by a crimp. Alternatively, the barrel is made from a plastic such as polypropylene, polyethylene or a cycloolefinic polymer (COC, COP). The barrel has a cylindrical portion connected to a neck portion. The crimp can be a metal crimp, for example an aluminum crimp according to ISO 8362-3 with a center hole allowing for passage of a needle through the septum. The crimp has a cylindrical skirt that is deformable for attachment to the neck portion of the barrel and the skirt is connected to an end wall having the center hole. The septum may be dimensioned after ISO 8362-2. The septum closes the neck portion of the barrel and is attached to the cartridge by plastically deforming the skirt of the crimp. The septum is made of an elastic material that can be penetrated and has a surface (inner surface) which may contact the liquid medicament and an outer surface which is surrounded by the center hole of the crimp. The surface of the septum opposite to the surface of the septum contacting the liquid medicament is sterile, and covered by a first area of a first continuous flexible strip that is attached to the crimp. The first continuous flexible strip forms a sterile barrier and thereby keeps the opposite surface of the septum in a sterile condition. The septum is made from an elastic material such as a rubber.

The fluid path unit comprises a cartridge holder and a fluid path compartment or containment (referred to as the compartment) comprising a needle or spike in an interior of the fluid path compartment. The cartridge holder may be formed as a housing or housing part forming the compartment defining an interior space. The fluid path may be in the interior space and comprises the needle or spike and a tubing connecting the needle or spike to a second needle which is configured to penetrate the skin of the patient upon use. The needle or spike is configured to penetrate the septum of the cartridge through a passage in the fluid path compartment, and the passage may be configured as an aperture in the housing. The needle or spike is configured such that an injection or insertion mechanism enables a linear movement of the needle or spike from an initial position inside the compartment through the passage to a second position outside of the compartment. The linear movement is spring driven, motor driven or driven by a manual force applied by a patient. The second position is the position defined by that the needle has penetrated the septum. The needle or spike of the fluid pad unit may be cylindrically shaped with a sharp end for penetrating the septum and made of steel or plastic.

The passage of the compartment may be closed by a second continuous flexible strip that is attached to the fluid path compartment and the second continuous flexible strip has a second area covering the passage forming a protective barrier and thereby keeping the interior of the fluid path compartment in a sterile condition. The second area may entirely cover the passage and is attached to a wall of the fluid path compartment.

Alternatively, the passage of the compartment and/or the septum is covered by a plurality of continuous flexible strips or by a plurality of parts of a continuous flexible strip, for example due to folding the strip. For example, a third strip having aseptic or antibacterial properties may be positioned between the first and second continuous flexible strips.

The cartridge of the assembly is inserted into the cartridge holder of the fluid path unit such that the septum of the cartridge is aligned with the passage of the fluid path compartment. Furthermore, the first and second continuous removable flexible strips may contact each other and be sandwiched between the septum and the fluid path compartment, and may be sandwiched between the end surface of the crimp of the cartridge and the wall of the compartment having the passage.

The first continuous flexible strip has a first free end and the second continuous flexible strip has a second free end, the free ends of the first and second strip are connected to the first and second areas of the respective strips. The cartridge is positioned in the cartridge holder such that the first and second free ends are arranged substantially parallel to another and are located adjacent from the passage. The first and second continuous flexible strips are removable from the cartridge and the fluid path compartment by simultaneously pulling the first and second free ends for, or thereby, establishing a sterile connection between the opposite surface of the septum and the interior of the fluid path compartment.

The assembly for an injection or infusion device may include a cartridge configured as a cylindrical barrel (e.g., constructed of glass) that defines a first axis, which is aligned with the axis of the spike or needle positioned within the interior of the compartment. The first and second free ends of the first and second continuous flexible strips adjacent to the passage are oriented substantially perpendicular to the first axis. In an alternative, the first and second free ends are oriented off-axis or inclined with respect to the first axis.

In embodiments, the assembly includes the cartridge and the fluid path unit, where the first and second continuous removable flexible strips contact each other and are sandwiched between the septum and the fluid path compartment. Both strips may be compressed or pressed to each other by a biasing element, where the biasing element may be a spring or ratchet acting on the barrel of the cartridge biasing the cartridge towards the fluid path compartment. The biasing element or ratchet element is positioned between a housing or a housing part (such as a housing of the fluid path unit) and an end surface surrounding the opening of the cartridge opposite to the shoulder, or the biasing element acts between the housing and the cylindrical wall surface of the housing, or acts on the neck portion or crimp of the cartridge. The biasing element may be at least one resilient element connected to the crimp and positioned between the crimp of the cartridge and the fluid path compartment, such as an O-ring, an elastic double sided adhesive tape or a flexible arm. The biasing element may also be connected to the compartment of the fluid path unit, for example to the wall having the passage and act towards the cartridge. The biasing elements, springs or flexible elements may exert forces oriented along the first axis. The two strips are pressed to each other such that there is a tight fit between the two flexible strips, and the at least two contacting surfaces of the two adjacent strips may be flush with each other. Upon strip removal, the dimensional gap left by the strips may be simultaneously closed by the biasing element moving the cartridge towards the compartment or by the biasing element present between the cartridge and the compartment, or by a biasing element moving the compartment, or a part thereof towards the cartridge.

Alternatively, the cartridge is not biased towards the fluid path compartment.

The first and second continuous flexible strips may be constructed or made of a porous membrane comprising polyethylene or polypropylene fibers, as an example Gore®Tex or Tyvek® membranes may be used. The porous membranes are permeable to sterilization gases, such as ethylene oxide gas or hydrogen peroxide gas. Alternatively, the membranes may be sterilized using heat or steam sterilization (autoclaving). Alternatively, the membrane is non porous for example a metal coated polymer film (barrier film) and the sterilization is done using gamma, X-ray, E-beam, heat or autoclaving.

The assembly for an injection or infusion device includes the cartridge and the fluid path unit, and the first area of the first continuous flexible strip is attached to an end surface of the crimp, such as the end wall of the crimp comprising the center hole. The dimensions of the first area of the first continuous flexible strip may be such that it entirely covers the center hole and preferably covers a part of the end wall of the crimp. The first area of the first continuous flexible strip is attached to the end surface of the crimp, such as an end wall, by heat sealing, an adhesive glue, a hot melt or by using double sided adhesive tape. The double sided adhesive tape is multilayered with at least one core layer and at least two adhesive layers. The core of the double sided adhesive tape may have elastic properties, and for example comprises an elastic foam (for example polyurethane, or a polyolefinic foam). The double sided adhesive tape may be ring shaped covering the end wall of the crimp surrounding the center hole. The ring is a continuous ring such that a closed border can be formed.

The cartridge comprising the sterile liquid medicament may be sterilized prior to assembling the assembly. For example the cartridge is sterilized using gas plasma, ETO sterilization, gamma, X-ray or E-beam prior to inserting the cartridge into the cartridge holder. During the sterilization, the surface of the septum that is opposite to the surface contacting the medicament is sterilized as the gases or ionizing radiation go through the first area of the first continuous flexible strip. The surface of the septum remains sterile as it is protected by the first area of the first continuous flexible strip. In case the strip is folded, the gases pass through a stack of strip layers.

The assembly with the first continuous flexible strip has the first area of the first continuous flexible strip connected to the free end of the strip by at least one U-shaped fold. The first continuous flexible strip may be sandwiched in the assembly between the cartridge and the fluid path unit, such as the compartment or housing of the fluid path unit.

Alternatively, there may be two or three folds connecting the first area with the free end such that multiple fold surfaces are sandwiched between the crimp of the cartridge and the passage. The first continuous flexible strip may be connected to, and at least partially covered by a protective cap prior to inserting the cartridge into the cartridge holder. The protective cap covers the first continuous strip to protect the strip, and the protective cap may keep the strip in a folded configuration. The protective cap enclosing the folded first continuous flexible strip may be attached to the crimp of the cartridge, for example by glue, heat welding, ultrasonic welding or by an elastic hook that is part of the cap. The cap may comprise a predetermined breaking point such that the cap can be released from the cartridge. The advantage of such a cap is that the first strip material may be protected from damage. The cartridge with its the crimp, septum, medicament, plug and the first continuous strip may be sterilized while the protective cap has already been mounted. Optionally, the protective cap has holes or an area (clearance or cut out) allowing for passage of the sterilization gases.

The assembly for the injection or infusion device comprising the cartridge and fluid path unit in which the second area of the second continuous flexible strip covering the passage is attached to the housing of the fluid path compartment by heat sealing, an adhesive glue, a hot melt, adhesive tape or by using double sided adhesive tape. The double sided adhesive tape may comprise an elastic core material that may be compressed during assembly, thereby providing a resilient force between the cartridge and the fluid path unit due to the elastic properties of the core. The double sided adhesive tape on the fluid path unit may be combined with the double sided adhesive tape present on the crimp of the cartridge for fixating the first continuous flexible strip.

The width and length of the second area of the second continuous flexible strip is such that the second area entirely covers the passage. The dimensions of the passage are such that the needle or spike of the fluid path can move through the passage.

The assembly of the cartridge and the fluid path unit wherein the fluid path unit is sterilized using gas plasma, ETO sterilization, gamma sterilization, E-beam sterilization or hydrogen peroxide gas sterilization prior to inserting the cartridge into the cartridge holder. During the sterilization process, the gases may pass through the second strip into the interior of the compartment holding the fluid path and sterilize the interior of the compartment including the fluid path. After sterilization with the sterilization gasses, the compartment is flushed to remove, for example, ETO residues. The compartment may have at least one other passage which is also protected by a film. The at least one other passage is configured for the second needle to move through that passage and insert into the patient's skin. The at least one other passage may be covered with a gas permeable film allowing for the sterilization gases to enter the interior or the at least one other passage may be covered by a gas barrier film. The interior of the compartment may remain sterile and protected from the environment, for instance by the second continuous strip covering the passage.

The second area of the second continuous flexible strip may be connected to the free end of the strip by at least one U-shaped fold, such as two U-shaped folds. The second area of the second strip, whether folded or not, may be covered by a second protective cap to protect the passage. The second protective cap may be glued, heat welded, ultrasonic welded or snap fitted onto the compartment, such as onto the wall of the compartment comprising the passage. The first and second caps are configured to allow for the free ends of the first and second continuous flexible strips to be adjacent from the first and/or second cap, e.g., a part of the continuous flexible strip is covered by the cap whereas the free end is not covered by the cap.

The assembly of the fluid path unit and the cartridge may involve inserting the cartridge into the cartridge holder in a non-sterile environment. Optionally, the first and second protective caps need to be removed before assembling the assembly.

In the assembly, the first and second free ends of the first and second continuous flexible strips may be oriented parallel to another and may be connected to each other, or to one or both of the first or second protective caps, or connected to a removable release liner protecting an adhesive layer configured for attaching the injection or infusion device to the skin of a patient. By removing the release liner from the adhesive layer the two continuous flexible strips may be simultaneously removed and the sterile connection between the septum of the cartridge and the interior of the compartment is established just before adhering the device to the skin of the patient. Alternatively, the two strips are removed one after another. As yet another alternative, another release liner or tape is removed from the device that is not intended to protect an adhesive layer. Removal of the another release liner or tape removes one or both of the continuous flexible strips.

The assembly for an injection or infusion device may be such that the needle or spike of the fluid path is configured to move through the passage in the housing of the fluid path unit and to penetrate the septum of the cartridge after withdrawing both flexible continuous strips. Removing the strips first establishes the sterile connection, and optionally, removing the strips may also activate the device, for example by activating a switch. The two flexible strips may be sandwiched between the cartridge and the fluid path unit and may abut each other and, further, may be compressed to each other. The compression may be supported by the resilient element acting on the cartridge holder and/or the resilient element present between the cartridge and the fluid path unit. The fact that both flexible strips are in abutment and in a compressed state, optionally supported by the resilient element(s), may fill the gap between the cartridge (end wall of the crimp) and the fluid path unit (wall of compartment comprising the passage) simultaneously upon removal of the strips. Each of the two strips may have a thickness between 0.05 mm and 0.25 mm or between 0.10 and 0.18 mm, or at 0.15 mm. The gap between the cartridge and the wall having the passage may vary between 0.10 and 1 mm upon removal of the strips. This gap may be closed during or immediately after strip removal by the resilient elements or members acting on the barrel of the cartridge towards the wall having the passage and/or acting between the crimp of the cartridge and the wall. Alternatively, the gap is not closed upon strip removal and the spike is inserted immediately through the septum after strip removal.

Activation by strip removal may also close an energy circuit of the device (for example by simultaneously removing an isolation foil from one or both of the battery terminals) which may be followed by activating (starting) the injection, for example by pressing a button. Or, alternatively, activation by removing the strips directly starts the injection procedure. The first and/or second continuous flexible strips may serve a dual purpose of establishing the sterile connection and simultaneously closing the electrical circuitry or starting the injection.

An injection or infusion device may include the assembly of the cartridge and the fluid path unit as described above.

A method for assembling the assembly for an injection or infusion device includes the steps of:

a) providing a cartridge comprising a sterile liquid medicament contained in a barrel, the cartridge being closed by a septum fastened to the barrel by a crimp, the surface of the septum opposite to the surface contacting the liquid medicament being sterile and covered by a first area of a first continuous flexible strip that is attached to the crimp, thereby keeping the opposite surface of the septum in a sterile condition.

b) providing a fluid path unit comprising a cartridge holder and a fluid path compartment comprising a needle or spike in an interior of the fluid path compartment, the needle or spike is configured to penetrate the septum of the cartridge through a passage in the fluid path compartment, wherein the passage is closed by a second continuous flexible strip that is attached to the fluid path compartment, the second continuous flexible strip having a second area covering the passage thereby keeping the interior of the fluid path compartment in a sterile condition.

c) inserting the cartridge in the cartridge holder of the fluid path unit such that the septum is aligned with the passage of the fluid path compartment and that the first and second continuous removable flexible strips contact each other and are sandwiched between the septum and the fluid path compartment, wherein the first continuous flexible strip has a first free end and the second continuous flexible strip has a second free end, the first and second free ends are arranged substantially parallel to another adjacent from the passage during insertion.

The method for assembling the assembly may further comprise the step of:

d) removing the first and second continuous flexible strips from the cartridge and fluid path compartment by simultaneously pulling the first and second free ends for establishing a sterile connection between the opposite surface of the septum and the interior of the fluid path compartment. Step d) may be performed by the user or step d) is done directly after assembly of the device in the factory.

The method may additionally comprise the following step of:

e) sterilizing the cartridge comprising the sterile liquid medicament using gas plasma or ETO sterilization prior to inserting step c). Step e) may be done using an empty cartridge or a full cartridge containing the medicament. Alternatively the sterilization is done using heat, autoclaving or ionizing radiation (gamma, E-beam or X-ray).

The method may additionally comprise the following step of:
f) sterilizing the fluid path unit using gas plasma or ETO sterilization prior to inserting step c). Alternatively the sterilization is done using heat, autoclaving or ionizing radiation (gamma, E-beam or X-ray).

The insertion step c) may be executed in a non-sterile environment, for example in a clean room. Alternatively step c) is performed in a sterile environment.

BRIEF DESCRIPTION OF THE DRAWINGS

FIG. 5a: Longitudinal section of FIG. 5b, FIG. 5b: Crimp of FIG. 5, free end unfolded, FIG. 5c: Crimp with flexible strip connected to the end wall having a first area covering the hole and a free end connected thereto via a U-shaped fold, free end connected to crimp by adhesive tape, FIG. 6a: Longitudinal section of FIG. 6b, FIG. 6b: Crimp with flexible strip, flexible strip protected by a cap and cap holds the strip in a folded configuration, FIG. 7b: Crimp of FIG. 6b, cap removed, FIG. 7a: Longitudinal section of crimp of FIG. 6b, free end unfolded, FIG. 8a: Crimp with flexible strip, free end releasable inserted into the first area of the strip, FIG. 8b: Longitudinal section of FIGS. 8a and 8c, FIG. 8c: Crimp with flexible strip, free end releasable inserted into the first area of the strip, FIG. 9a: Crimp with flexible strip connected, strip material with perforated pattern, free end partially released from the first area, FIG. 9b: Crimp with flexible strip connected, strip material with perforated pattern, free end released from the first area, first area may be removed by pulling the free end, FIG. 9c: Crimp with flexible strip connected, strip material with perforated pattern for releasing the free end, FIG. 10a: Crimp of FIG. 10c, partially unfolded strip, FIG. 10b: Crimp of FIG. 10, first area of strip partially removed from crimp, FIG. 10c: Crimp with flexible strip, first area connected to the free end via two U-shaped folds, FIG. 11a: Crimp with flexible strip attached to the double sided adhesive tape, FIG. 11b: Longitudinal section of FIG. 11a, FIG. 11c: Crimp with ring shaped double sided adhesive tape attached to the end wall, FIG. 9c, FIG. 12c: Unfolded strip. Configuration of FIG. 8, FIG. 13a: Configuration of FIG. 13, strip partially unfolded, FIG. 13b: Cartridge with crimp and flexible film connected to the crimp via a ring of double sided adhesive tape, FIG. 14a: Cartridge with crimp, strip and cap, FIG. 14b: Cartridge of FIG. 14, cap removed, the free end of the strip is connected to the cap, FIG. 14c: Longitudinal section of cartridge with septum, crimp and flexible strip covered by a cap, FIG. 15: Fluid path unit with a compartment or containment for the spike and passage. The passage in the compartment or containment closed by a second flexible strip material that is attached to the compartment or containment using double using double sided adhesive tape, FIG. 16a: Assembly of FIG. 16, the two ends of the two flexible strip removed from the assembly, FIG. 16b: Magnified view of FIG. 16c, FIG. 16c: Assembly of cartridge inserted into the fluid path unit. The crimp of the cartridge being covered by the first strip, the passage of the compartment or containment being covered by the second strip. First and second strips directly connected to the crimp and compartment or containment, FIG. 18: Assembling the assembly of the cartridge and the fluid path unit; insertion from the end of the cartridge holder, FIG. 19: Assembling the assembly of the cartridge and the fluid path unit; sideway insertion of the cartridge into the holder. Cartridge holder has a resilient element for biasing the cartridge towards the compartment.

DETAILED DESCRIPTION

Figure 1:
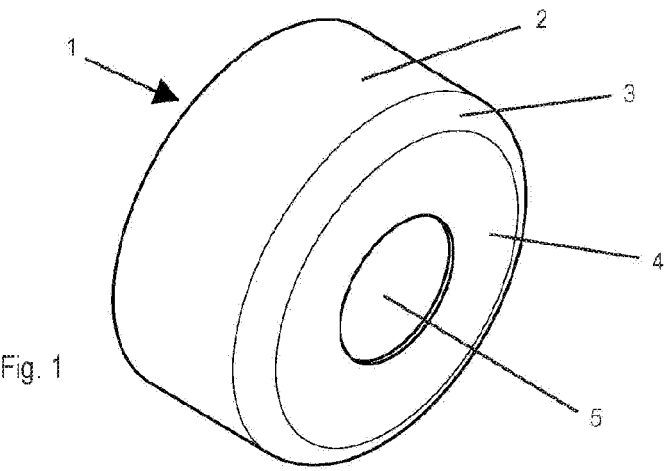
FIG. 1: Crimp with skirt, end wall having a center hole.

In FIG. 1, a crimp (1), also called a crimp cap, is shown having a cylindrical section (2) and an end wall (4) which is connected to the cylindrical section (2) via a circumferential facet (3). The end wall (4) has a hole (5) or passage in the center. The crimp (1) shown in FIG. 1 is in the non-deformed state. The cylindrical section (2) can be plastically deformed, for example, to hold a septum to a cartridge and close the cartridge. The crimp (1) is made from a plastically deformable material, for example, a metal such as steel or aluminum. Alternatively, the crimp is made from a plastic material such as polypropylene (PP), polyethylene (PE), polyphenylsulfone (PPSU), polyoxymethylene (POM), polyether ether ketone (PEEK), polystyrene (PS), polycarbonate (PC), polyethylene terephthalate (PET), or a heat shrinkable material made from a cross-linked polymer.

Figure 2B:
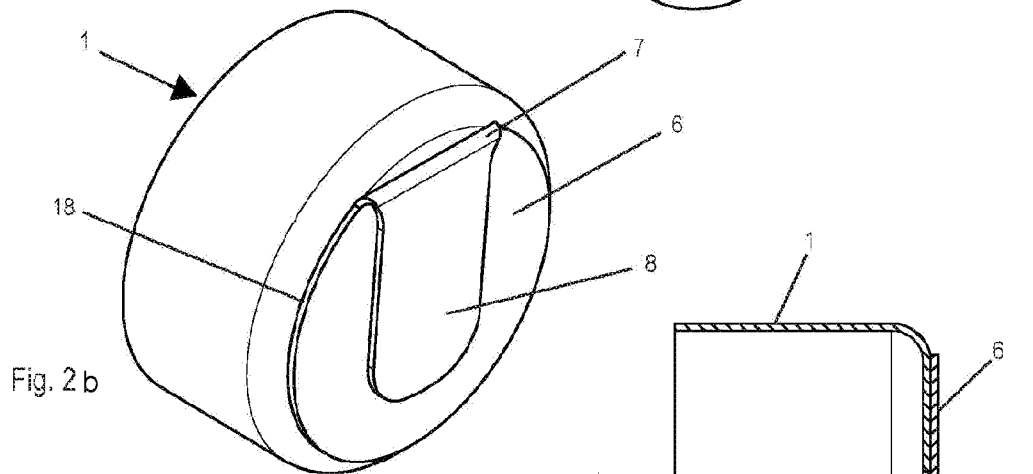
FIG. 2b: Crimp with flexible strip connected to the end wall having a first area covering the hole and a free end connected thereto via a U-shaped fold.
Figure 2A:
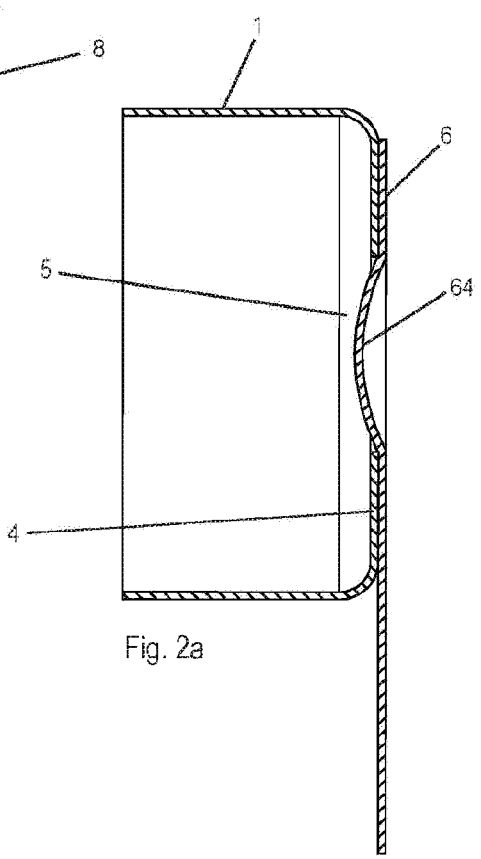
FIG. 2a: Crimp with flexible strip connected to the end wall, concave part of strip covering the hole of the crimp.

A first continuous flexible strip (18) is attached to the end wall (4) of the crimp (1) as shown in FIGS. 2a and 2b. The first continuous flexible strip material may be made from Tyvek®, a non-woven flexible sheet comprising polyethylene fibers, which allows for passage of gases such as ethylene oxide or hydrogen peroxide gas but prevents the passage of germs and forms a sterile barrier. The first continuous flexible strip material (18) may be pre-coated on one side with an adhesive, an adhesion promotor or a coupling agent which facilitates the adhesion of the Tyvek® film to another surface. The first continuous flexible strip (18) comprises a first area (6) which covers the hole (5) in the center of the end wall (4) of the crimp (1) and a free end (8). The rim of the first area (6) of the flexible strip (18) is attached to the end wall (4) of the crimp (1), either by heat sealing, gluing, ultrasonic welding, heat welding or a hot melt. The adhesive may also be provided as a separate coating on the Tyvek® film (additional to the pre-coating) or is applied separately onto the end wall (4) of the crimp (1). Optionally, the end wall (4) is pre-coated with an adhesive layer or an adhesion promotor. As a further option, the surfaces of the crimp and/or Tyvek® film are treated with a plasma (for example Ozone plasma) to improve the adhesion. The free end (8) and the first area (6) of the strip (18) may be connected to each other by a U-shaped fold (7).

In FIG. 2a, an alternative configuration is presented for the arrangement of the first continuous flexible strip (18) on the crimp (1). The section of the strip (18) covering the hole (5) of the end wall (4) is convex shaped (64). The first continuous flexible strip (18) is attached to the end wall (4) and during the attachment the convex shape is formed, for example by a matching concave shaped protrusion on the attachment tool. The advantage of the convex shaped part (64) is that any dimensional changes, for example due to stress relaxation, during subsequent processing steps or during storage, are compensated for by the extra material therewith avoiding mechanical stress on the connection between the end wall (4) and the strip (18).

Figure 3B:
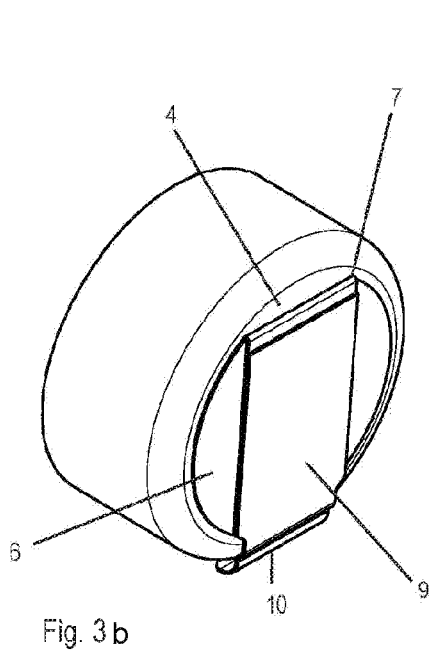
FIG. 3a: Longitudinal section of FIG. 3b, FIG. 3b: Crimp with flexible strip connected to the end wall having a first area covering the hole and a free end connected thereto; the free end being connected to the skirt of the crimp by an additional foil (Tyvek®)
Figure 3A:
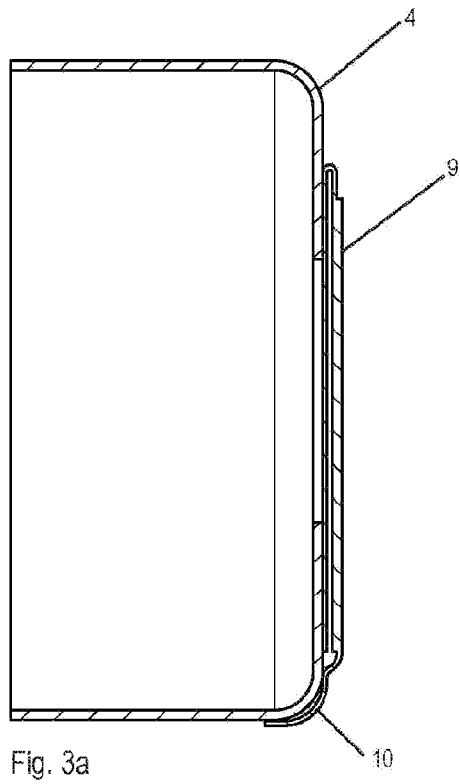
Figure 4B:
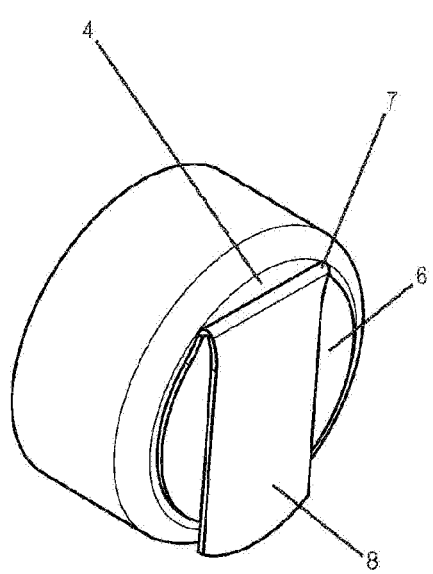
FIG. 4b: Crimp with flexible strip connected to the end wall having a first area covering the hole and a free end connected thereto via a U-shaped fold.
Figure 4A:
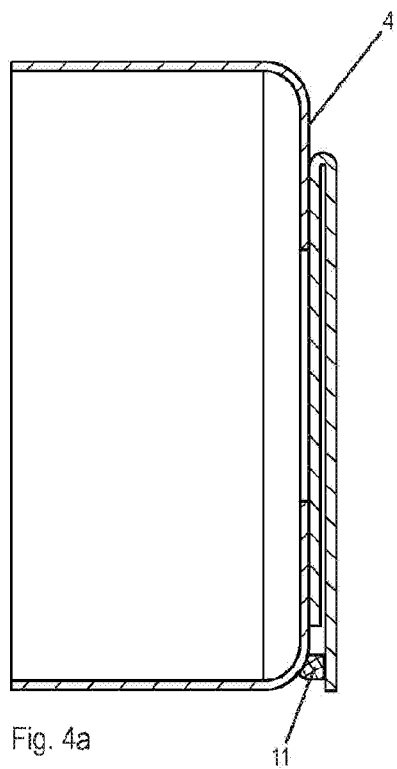
FIG. 4a: Longitudinal section of FIG. 4b, showing adhesive connection.

The free end (8) of the first continuous flexible strip (18) may be connected to the crimp (1) as shown in FIGS. 3a to 6b. The advantage of the free (8) end being connected to the crimp is that the free end is not loose, improves handling and cannot get entangled with other parts, for example if the crimps (1) with the strips are produced in bulk. In FIGS. 3a and 3b, the free end (8) of the strip is connected to a top layer (9), which itself may also be made of Tyvek®, and the end of the top layer (9) is connected to a connecting area (10) located on the facet (3) or cylindrical section (2) of the crimp (1). In FIGS. 4a and 4b, the end of the free end (8) of the first continuous flexible strip is attached by a spot weld, or adhesive connection point (11). In FIGS. 5a-5c, the free end (8) of the strip (18) is connected to crimp using adhesive tape (12), and FIG. 5b shows the free end unfolded.

The first continuous flexible strip (18) may be covered by a protective cap (13) to prevent damage to the flexible strip during handling (FIGS. 6a and 6b). The cap (13) is releasably attached to the crimp and may be snap fitted onto the crimp (1) or may be connected to the crimp by an adhesive. For example the cap (13) comprises connectors (15) which are glued or welded to the crimp. The connectors (15) have predetermined breaking points (16) for releasing the cap (13) from the crimp. The cap (13) may have a passage (17) in the end wall (14) to facilitate gas sterilization and/or insertion of the needle through the strip (18). The strip (18) may be unfolded after the cap (13) has been released from the connectors (15), as shown in FIGS. 7a and 7b or FIG. 10a. The cap (13) may also have a cut out such that the free end (8) is adjacent to the cap (13) when the cap is attached to the crimp, e.g. the free end (8) is not covered by the cap (13). This enables removal of the strip (18) when the cap (13) is still attached to the crimp (1).

In FIGS. 8a, 8b and 8c, the end of the folded flexible continuous strip (18) is releasably attached with the first area (6) in the following manner: The first area (6) of the strip (18) has an extension (19) with a passage (20) configured to receive an extension (21) of the free end (8) of the strip (18). The free end (8) is folded through the passage (20) of the first area (6) of the strip (18). The advantage is that this does not require additional glue or welding. Alternative solutions for keeping the first continuous flexible strip in a folded configuration are presented in FIG. 12a.

The free end (8) of the first continuous flexible strip (18) may also be formed from a single layer compared to the at least one time folded layers presented above. In FIGS. 9a, 9b and 9c, the first continuous flexible strip is a disc shaped (22) single layer having, in this example, two perforation lines (23, 24) (and see FIG. 12b). Once the ring-shaped free end (25) has been released by tearing the first perforation line (23), the ring is available for further pulling to tear the second perforation line (24) thus forming the free end of the strip (8), see FIGS. 9a to 9c.

An example of a crimp (1) with a first continuous flexible strip (18) having two folds (7, 7') is shown in FIG. 10c. Once the free end (8) has been folded back once (FIG. 10a), the center hole (5) in the end wall (4) of the crimp can be opened (FIG. 10b) by pulling the free end (8).

The first continuous flexible strip (18) may also be attached to the end wall (4) of the crimp (1) using double sided adhesive tape (FIGS. 11a, 11b and 11c). A ring shaped double sided adhesive tape (26) is attached to the end wall (4) of the crimp (1). The other side of the double side adhesive tape is available for attaching the first area (6) of the first continuous flexible strip (18). The core (27) of the ring shaped double sided adhesive tape (26) optionally is made of an elastic material. The advantage being that the core may be compressed and compensate for dimensional tolerances and/or the gap that is created once the first continuous flexible strip (18) has been removed. The ring shaped double sided adhesive tape (26) may be combined with another elastic or resilient element, for example an elastic element (O-ring) that is present on a counter surface adjacent to the end wall (4) of the crimp (1).

Figure 12:
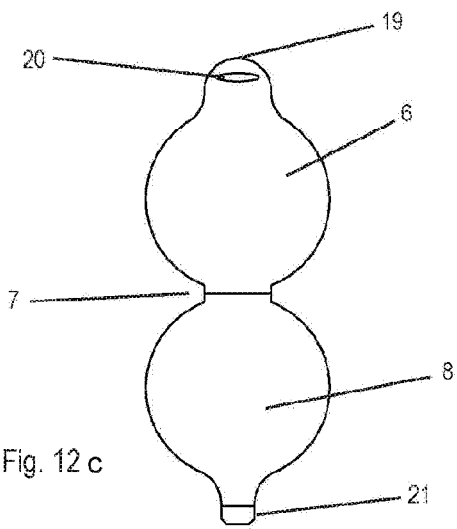
Figure 12A:
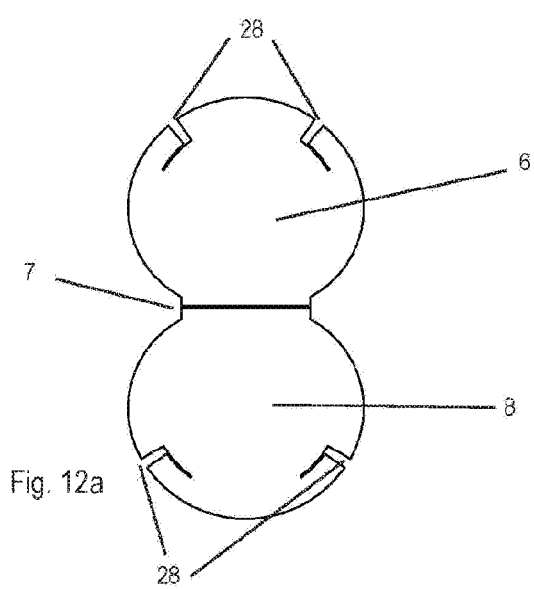
FIG. 12a: Unfolded strip with cut-outs for releasable, interleaved connection.
Figure 12B:
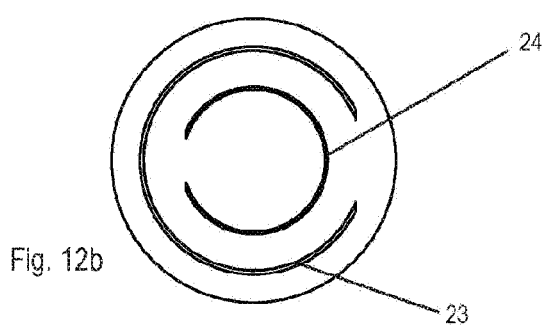
FIG. 12b: Strip, pre perforated, configuration

Other examples for designs for the first continuous flexible strip (18) are shown in FIGS. 12a, 12b and 12c. For example, in FIG. 12a, the first area (6) and second area (8) of the strip can be interwoven with flexible arms (28), having the advantage of controlling the free end (8) of the strip to keep the strip into the folded configuration without the need of an adhesive. In FIG. 12b, two perforation lines (23, 24) are shown and described supra in connection with FIGS. 9, 9a and 9b.

FIGS. 13a and 13b show a cartridge (29) comprising a barrel (32) defining a longitudinal axis having a neck portion (30) for fixation of a not shown septum to the neck using the crimp (1). The barrel may be filled with a liquid medicament and closed by a plug (not shown) which enters the barrel via opening (31) that is opposite to the neck portion (30). The crimp (1) of the cartridge is closed by the first continuous flexible strip (8). The cartridge can be defined either as a) the assembly of the barrel (32), with the septum, the crimp (1) and the first continuous flexible strip (8), as being an empty cartridge, or b) the assembly further comprising the plug and the liquid medicament, e.g., a filled cartridge. The first continuous flexible strip (8) is in the example presented in FIG. 13b attached to the crimp (1) using double sided adhesive tape. Alternatively, the strip (8) is heat sealed, glued or ultrasonically welded to the end wall (4) of the crimp (1). In FIG. 13a, the first continuous flexible strip (8) has been unfolded such that the free end (8) is adjacent to the crimp (1).

A longitudinal section of an empty cartridge is shown in FIG. 14c. The septum (33) is connected to the neck (30) by the crimp (1). The septum (33) has an inner surface (34) directed towards the open end (31) of the barrel (32), e.g. which is intended for contacting the liquid medicament. The septum (33) has an outer surface (35) which is opposite to the inner surface (34) and the outer surface is surrounded by the center hole (5) of the end wall (4) of the crimp (1). The outer surface (35) is covered by the first continuous flexible strip (18) and, in this example, protected by a cap (13). A 3-dimensional view of the cartridge (29) with the cap (13) attached to the crimp or with the cap (13) released from the crimp (1) is presented in FIGS. 14a and 14b, respectively.

A cross section of a fluid path unit (46) is shown in FIG. 15, comprising a compartment or containment (36) (referred to as the compartment) connected to a cartridge holder (37). The compartment (36) and cartridge holder (37) may be constructed as one unit, for example using injection molding of a plastic. The cartridge holder may have a viewing window (39). The compartment (36) is shaped as housing with walls (42) forming an interior (47). A fluid path is enclosed in the interior (47) comprising a tubing connecting a needle designed for injection into the patient's skin, to a needle or spike (40) that is intended for penetrating the septum (33) of the cartridge. In FIG. 15, the spike (40) is shown whereas the tubing and injection needle for piercing the skin are not shown. The spike (40) defines a longitudinal axis that is aligned with the longitudinal axis of the cartridge (29) once the assembly of the cartridge and fluid path unit (46) has been established. A connecting wall (43) connects the compartment (36) to the cartridge holder (37). A passage (38) also called aperture, opening or hole which are all considered equivalent, connects the interior (47) of the compartment (36) with an interior (48) of the cartridge holder (37). The axis of the spike (40) is oriented and positioned such that the spike (40) can move through the passage (38). The spike (40) is part of a spike holder (41) which is configured to move the spike (40). The holder and the spike may be injection molded as one unit or a hollow steel needle is glued into the holder.

The passage (38) of the connecting wall (43) is covered by a second continuous flexible strip (49) which closes the passage of the compartment (36), more specifically, a second area (60) covers the passage. The second continuous flexible strip (49) may be constructed from the same material as the first continuous flexible strip (18) and may form a sterile barrier. The second continuous flexible strip (49) may be attached to the compartment (36), more particularly to the connecting wall (43) of the compartment (36) using the same attachment methods as described above for the first continuous flexible strip material (18), e.g. by gluing, heat welding, heat sealing, ultrasonic welding or a hot melt. In the example presented in FIG. 15, the second continuous flexible strip (49) is attached to the compartment (36) using a double sided adhesive tape (50). The shape, folds, and methods to prevent unfolding the second continuous flexible strip (49) may be identical as described and presented in FIGS. 1 to 6b and FIGS. 8a to 12c for the first continuous strip (18). Thus the second area (60) of the second continuous flexible strip (49) may be connected by at least one U-shaped fold to a free end (8') of the strip. A protective cap (13) as described in FIGS. 6c and 14 may also be applied to the second continuous flexible strip (49).

The fluid path unit (46) has a lateral opening (44) which may be located between the compartment (36) and the cartridge holder (37). The free end (8') of the second continuous flexible strip (49) may pass through the passage (44) such that the free end (8') of the strip (49) is adjacent to the passage (38) and outside of the fluid path unit (46). The free end (8') may be releasably attached to the passage (44) of the fluid path unit to fixate the position of the free end (8') during handling.

The fluid path unit (46) comprising the compartment (36) with the interior (47) comprising the fluid path may be sterilized after the passage (38) of the connecting wall (43) of the compartment (36) has been closed with the second continuous flexible strip (49). Another aperture (62) or opening (FIG. 21), designated for passage of the needle that is inserted into the skin is closed by a film as well, which may be permeable to gases. The fluid path unit (46) may be sterilized using gas sterilization such as ETO or hydrogen peroxide sterilization. The sterilization step may be done before insertion of the cartridge (29) into the fluid path unit (46), alternatively, the assembly of fluid path unit and cartridge is sterilized as a unit.

The assembly of the cartridge (29) with the septum (33) attached by the crimp (1) having the first continuous flexible strip (18) and the fluid path unit (46) with the compartment (36) closed by the second continuous flexible strip (49) is shown in FIG. 16c and in detail in FIG. 16b. The first and second continuous flexible strips (18, 49) both have one U-shaped fold connecting the first areas (6, 60) of the first and second strips to both free ends of the strips (8, 8'). The cartridge (29) is closed by a plug (51) for enclosing the liquid medicament in the barrel between the plug (51) and the septum (33). The folded surfaces of the first and second continuous flexible strips (18, 49) may be compressed between the crimp (1) of the cartridge and the passage (38), or connecting wall (43). The free ends (8, 8') that are not attached to the crimp (1) or compartment (36) may abut each other as the strips are compressed towards each other. Alternatively, only a part of the free ends (8, 8') of both strips abuts each other as the free ends (8, 8') may be connected to different parts or at different positions on the same part, for example connected to a release liner that is explained below. The free ends (8,8') of both flexible continuous strips (18, 49) may be oriented parallel to another and are next to, or adjacent to the passage (38) of the connecting wall (43) and extend through the lateral opening (44) of the fluid path unit (46). Both flexible strips (18, 49) can be removed from the crimp (1) and the compartment (36) by pulling both free ends (8,8') of the strips. Both strips (18, 49) may be removed simultaneously from the fluid path unit (46), as presented in FIG. 16a, bringing the sterile outer surface (35) of the septum (33) in a sterile connection with the sterile interior (47) of the compartment (36) of the fluid path unit (46). The spike (40) can now penetrate the sterile outer surface (35) of the septum (33). Optionally the free ends (8, 8') are connected to each other to facilitate strip removal.

The first and second continuous flexible strips have a certain thickness, for example 0.15 mm, thus at least a gap of 0.30 mm may exist between the connecting wall (43) and the end wall (4) of the crimp (1). In one embodiment, this gap is not closed and the spike (40) is inserted shortly after removing the flexible strips to ensure sterility of the outer surface (35) of the septum (33). The outer surface (35) of the septum can also be designated as the surface of the septum (33) that is opposite to the surface (34) of the septum contacting the medicament.

The gap which exists between the end wall (4) of the crimp (1) and the connecting wall (43) may also be closed by a resilient element. The first example that may be used as resilient element is the septum (33) of the cartridge (29). The cartridge (29) may be inserted in the cartridge holder (37)

such that the crimp (1) is pushed against the connection wall (43) and moves relative to the open end of the cartridge such that the septum (33) is compressed between the crimp (1) and the barrel (32). When the two continuous flexible strips (18, 49) are removed, the elastic properties of the septum ensures that the end wall (4) of the crimp (1) is moved, closes the gap and abuts with connection wall (43) of the compartment (36) of the fluid path unit (46).

Figure 20:
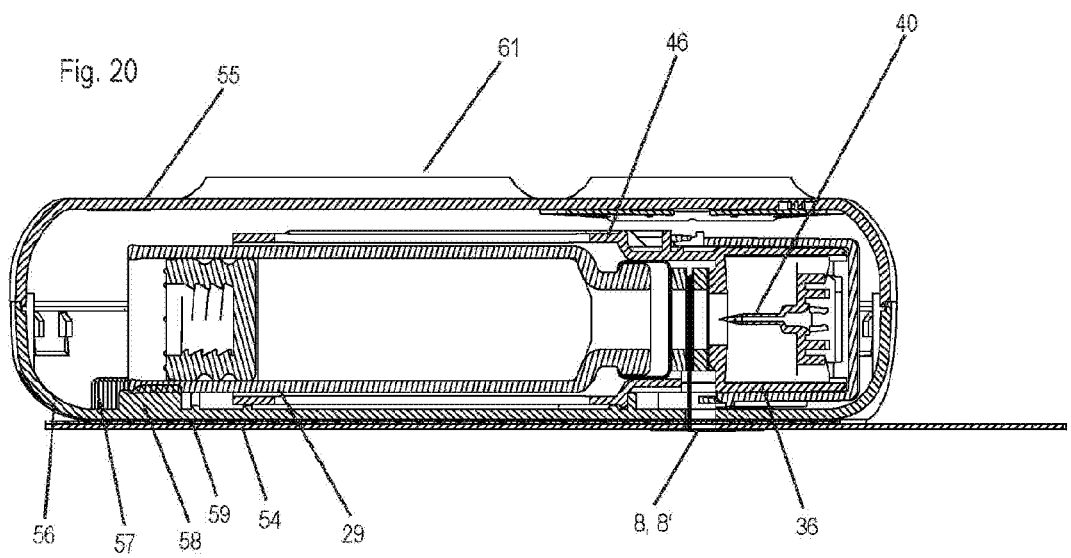
FIG. 20: Patch device comprising the assembly of the cartridge and fluid path unit, the cartridge is biased by a ratchet towards the compartment. The free end of the flexible strips are connected to a release liner of the patch device.

Other options to close the gap between the crimp (1) and the compartment (36) upon strip removal are i) the use of resilient elements between the crimp (1) of the cartridge and the compartment (36), an example is the use of elastic double sided adhesive tape (FIG. 17*b*); ii) an elastic element, such as a spring (52) acting on the barrel of the cartridge towards the compartment (FIG. 19); or iii) a ratchet mechanism (57, 58) biasing the cartridge towards the compartment (FIG. 20). Other options or combinations of the above mentioned options can be implemented by the skilled person.

Figure 17B:
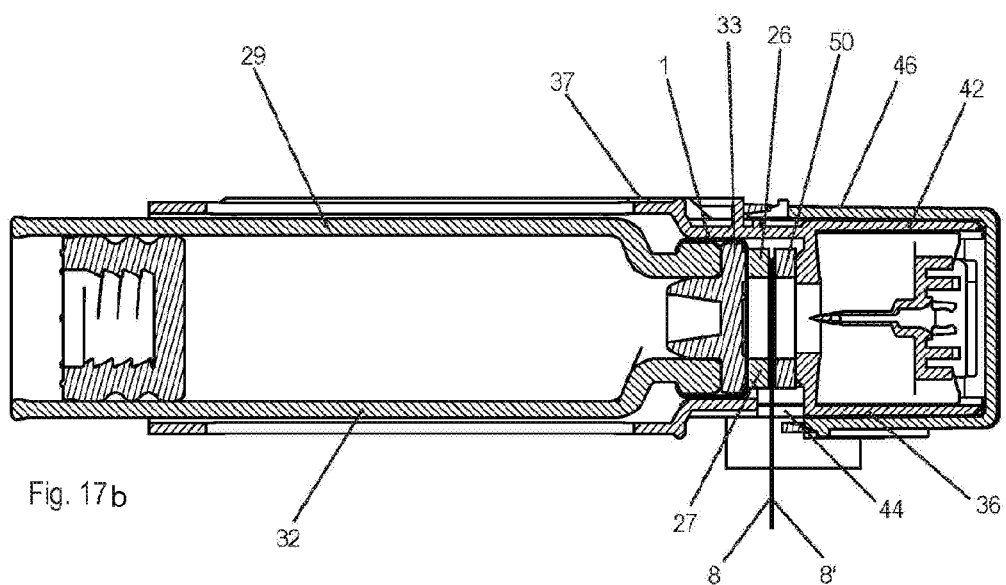
FIG. 17b: Assembly of cartridge inserted into the fluid path unit. The crimp of the cartridge being covered by the first strip, the passage of the compartment being covered by the second strip. First and second strips attached using double sided adhesive tape.
Figure 17A:
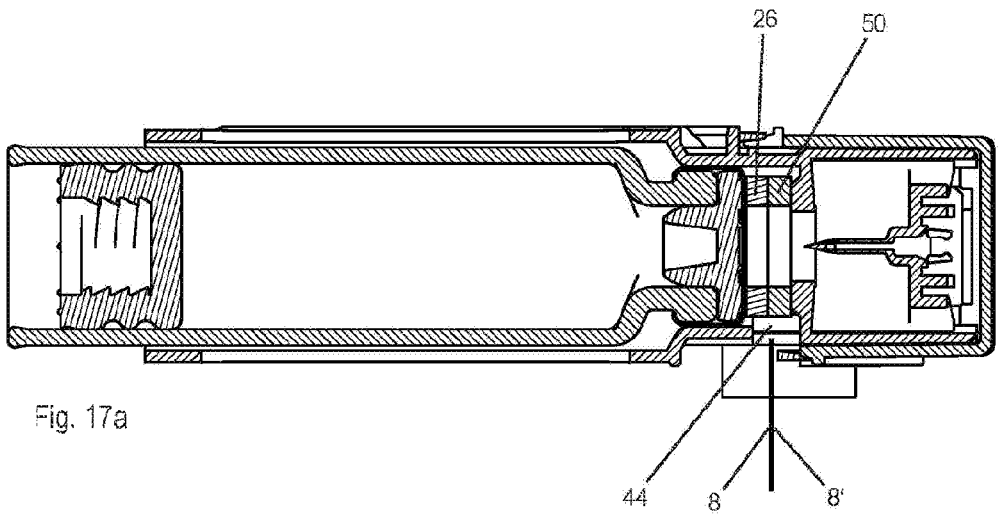
FIG. 17a: Assembly of FIG. 17b, the two ends of the two flexible strip removed from the assembly.

In FIG. 17*b*, the assembly of the cartridge (29) and the fluid path unit (46) comprising the compartment (36) and the cartridge holder (37) is presented. The first and second continuous flexible strips are attached to the crimp (1) of the cartridge and the connecting wall (43) of the compartment (36) using ring shaped double sided adhesive tapes (26, 50). The adhesive tapes have an elastic core (27) which is compressed during insertion of the cartridge (29). The cartridge (29) may be fixated to the cartridge holder (37) using a cartridge fixator, for example a ratchet (see also FIG. 20), a glue, a wedge shaped insert between the cartridge and the cartridge holder, a spring (see FIG. 19), a screw type connection or by plastically deforming a rib or another piece of metallic or plastic material that is part of the cartridge holder. The axial position of the barrel (32) of the cartridge is fixated relative to the cartridge holder and thus also relative to the connection wall (43) such that the elastic cores of the double sided adhesive tapes (26, 50) are in a compressed state during storage. Upon removal of the first and second continuous flexible strips by pulling both free ends (8, 8') of the strips (FIG. 17*a*), the gap will be closed simultaneously by the elastic recovery of the two ring shaped double sided adhesive tapes (26, 50) and therefore ensure for immediate closure of the gap without the risk of non-sterile contamination of the outer surface (35) of the septum (33) before insertion of the spike (40).

As an alternative, only one of the two continuous flexible strips is attached to the crimp or connection wall using double sided adhesive tape. Alternatively only one strip is attached using the tape, and the strip on the counter surface is directly attached to the surface without the tape.

As yet another alternative, the elastic members between the crimp of the cartridge and the compartment (36) is an O-ring, or an element supported by a spring that extends from the connection wall (43) of the compartment (36).

The method for assembling the assembly of the cartridge (29) and the fluid path unit comprising the cartridge holder (37) is shown in FIG. 18. The cartridge (29) having the first continuous flexible strip (18) (not shown) attached to the crimp (1) may be sterilized prior to insertion into the cartridge holder, this to ensure that the outer surface (35) of the septum is sterile. The cartridge (29) is aligned with the longitudinal axis of the barrel (32) towards the center of the opening (45) of the cartridge holder (37). The cartridge is then inserted with the crimp (1) ahead into the cartridge holder (37) such that the free ends (8, 8') of the first and second continuous flexible strips are oriented parallel and flush to another. The cartridge may be fixated using an appropriate cartridge fixation mechanism as described above, thereby the two continuous flexible strips (18, 49) may be compressed. The free ends (8, 8') may be guided through the lateral opening (44) of the fluid path unit (46). After assembling the assembly of the cartridge and the fluid path unit, the other components such as drive unit, battery holder, electric motor and external housing(s) may be used for assembly of the injection or infusion device.

The cartridge (29) may also be inserted laterally into the cartridge holder (37) of the fluid path unit (46) as shown in FIG. 19. FIG. 19 shows a spring (52) which is positioned between an end wall (63) of the cartridge holder (37) and a spacer (53). After insertion of the cartridge (29), the spring biases the cartridge (29) towards the compartment (36) via the spacer (53). The spacer (53) may be a ring that engages the end section (31) of the barrel of the cartridge. After insertion of the cartridge (29) and removing the first and second continuous flexible strips (18, 49) (not shown), the gap created by the strip removal is closed by an axial shift of the cartridge. In this example a separate coil spring made of metal is used. Alternatively plastic springs are used. As another alternative, the end wall (63) is made as a separate screw cap that is screwed onto the cartridge holder (37). In yet another alternative, the end wall (63) is slid axially after cartridge insertion to bias the cartridge (29) towards the compartment (36) and the cap is subsequently glued to the cartridge holder (37). In another example, the cap with the end wall (63) comprises an asymmetric teething which engages an asymmetric teething on a housing part or on the cartridge holder to form a one-way ratchet. After insertion of the cartridge, the cap is positioned such that the ratchet is adjusted to bias the cartridge in the cartridge holder.

The filled cartridge with the first continuous flexible strip (18) and the fluid path unit (46) may be sterilized separately before assembly. The assembling of the assembly may be done in a non-sterile environment.

Alternatively, the crimp (1) with the first continuous flexible strip (18) is sterilized as a separate part and subsequently assembled with the cartridge comprising the septum (33) and the cartridge may be empty or filled. The assembly of the crimp with the cartridge may be done in a sterile environment.

The removal of the first and second continuous flexible strips may be done after the assembly of the fluid path unit and cartridge has been assembled with the other units such as the drive unit, housing, motor, battery package, control unit and the like, to form the assembled device. The first and second continuous flexible strips may be removed by the user just before medicament administration. Alternatively, the first and second continuous flexible strips are removed after assembling the assembly of the fluid path and the cartridge, but before assembling the final device with the other components.

If a protective cap (13) protects the first and/second continuous flexible strips (18, 49), then the protective cap(s) (13) may be removed before assembling the cartridge with the fluid path unit.

An example of an assembled a patch device (61), is presented in FIG. 20. The assembly comprising the cartridge (29) and the fluid path unit (46) is enclosed by a housing cover (55) and a bottom housing (56). The bottom housing (56) may comprise the opening for the needle that is inserted in the patient's skin. The cartridge (29) is biased towards the compartment (36) by a ratchet part (57) having asymmetric teeth that is axially shifted and ratchets against a counter ratchet (58) that is part of the bottom of the housing (56) until the desired position for the cartridge has been reached.

The first and second continuous flexible strips are attached respectively to the crimp and compartment by double sided adhesive tape; the other attachment means (heat sealing, glue, heat welding, ultrasonic welding) can also be used in the device of FIG. 20. The patch device (61) is attachable to the skin of a patient using an adhesive layer (59) which is applied to the bottom (56) of the device. The adhesive layer is protected by a release liner (54), which is a layer covering the adhesive layer (53). The user removes the release liner (54) just before attaching the device to the skin. The release liner (54) may be connected to both free ends (8, 8') of the first and second continuous flexible strips (18, 49), thus by removing the release liner (54) also both strips are removed to establish the sterile connection between the outer surface (35) of the septum (33) of the cartridge (29) and the fluid path enclosed in the compartment (36). Optionally, the electronic circuitry of the infusion device is powered as well by removing the release liner (54) for example by removing an isolation paper between the terminal of a battery and the electronic circuitry. The edges of the passage or aperture (62) for the needle may be smooth, rounded and/or comprise a facetted face to reduce friction between the strips and the housing upon removal and/or prevent damage to the strips.

Figure 21:
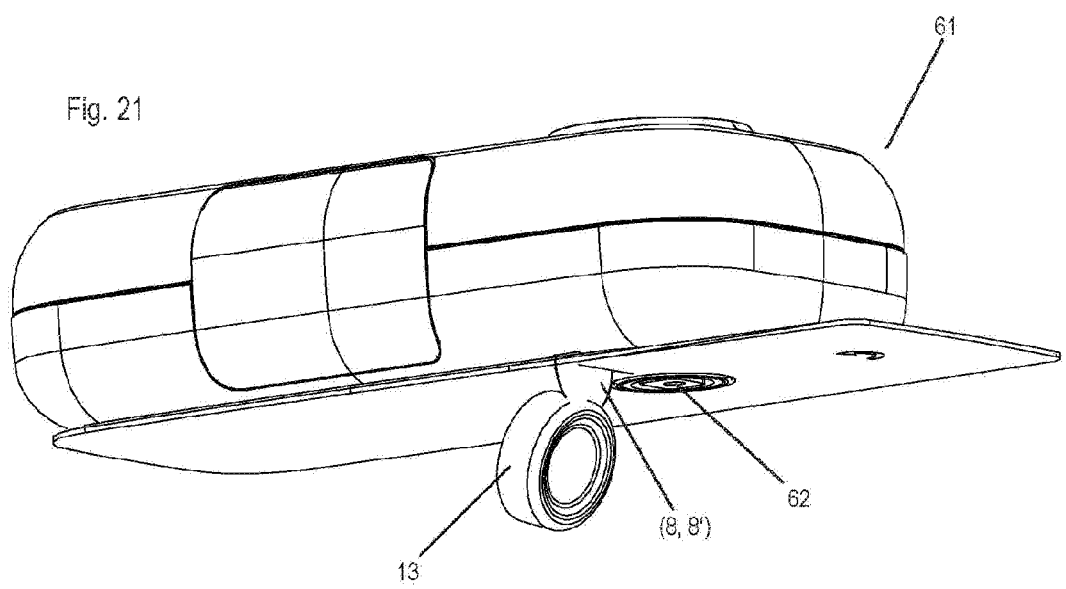
FIG. 21: Patch device comprising the assembly.

In FIG. 21, an infusion device (61) is presented where the protective cap (13) covering the first or second continuous flexible strip is used to remove the strips since the free ends (8, 8') are connected to the cap (13). The bottom of the housing comprises an aperture (62) for the needle that is intended for skin insertion. The cap (13) may cover the passage or aperture (62) during storage.

PART ANNOTATION

| | |
|---|---|
| 1) | Crimp |
| 2) | Skirt section, cylindrical section |
| 3) | Facet |
| 4) | End wall |
| 5) | Center hole, passage |
| 6) | First area of strip |
| 7) | Fold |
| 7') | Second fold |
| 8) | Free end of strip |
| 8') | Free end of second strip |
| 9) | Top layer |
| 10) | Connecting area |
| 11) | Weld, adhesive connection |
| 12) | Adhesive tape |
| 13) | Cap |
| 14) | End wall cap |
| 15) | Connector |
| 16) | Predetermined breaking point shaped |
| 17) | Passage, hole |
| 18) | First continuous flexible strip |
| 19) | Extension first area |
| 20) | Passage |
| 21) | Extension free end |
| 22) | Disc shaped film |
| 23) | First perforation line |
| 24) | Second perforation line |
| 25) | Ring shaped free end |
| 26) | Ring shaped double sided adhesive tape |
| 27) | Core strip |
| 28) | Flexible arm |
| 29) | Cartridge |
| 30) | Neck portion of the cartridge |
| 31) | Open end opposite to the neck portion |
| 32) | Barrel |
| 33) | Septum |
| 34) | Inner surface |
| 35) | Outer surface |
| 36) | Compartment or containment |
| 37) | Cartridge holder |
| 38) | Passage |

PART ANNOTATION -continued

| | |
|---|---|
| 39) | Viewing window/Insertion window |
| 40) | Spike, needle |
| 41) | Spike holder, needle holder |
| 42) | Wall, housing |
| 43) | Connecting wall |
| 44) | Lateral opening |
| 45) | Opening cartridge holder |
| 46) | Fluid path unit |
| 47) | Interior of compartment or containment |
| 48) | Interior cartridge holder |
| 49) | Second flexible continuous strip |
| 50) | Double sided adhesive tape - ring |
| 51) | Plug |
| 52) | Spring |
| 53) | Spacer |
| 54) | Release liner |
| 55) | Housing cover |
| 56) | Bottom housing |
| 57) | Ratchet |
| 58) | Counter ratchet housing |
| 59) | Adhesive |
| 60) | Second area second continuous flexible |
| 61) | Infusion device, patch device |
| 62) | Passage for needle |
| 63) | End wall/cap |
| 64) | Concave part of strip |

What is claimed is:

1. An assembly for an injection or infusion device, the assembly comprising a cartridge for a sterile liquid medicament, formed as a barrel, the cartridge being closed by a septum fastened to the barrel by a crimp, wherein a first surface of the septum opposite a second surface contacting the liquid medicament is recessed from a surface of the crimp, is sterile and is covered by a first area of a first continuous flexible strip, the first area of a first continuous flexible strip being attached to the surface of the crimp without contacting the first surface of the septum, thereby keeping the first surface of the septum in a sterile condition; and a fluid path unit comprising a cartridge holder and a fluid path compartment comprising a needle or spike in an interior of the fluid path compartment, wherein the needle or spike is configured to penetrate the septum of the cartridge through a passage defined in a surface of the fluid path compartment, wherein the passage of the fluid path compartment is closed by a second continuous flexible strip attached to the surface of the fluid path compartment, the second continuous flexible strip comprising a second area covering the passage thereby keeping the interior of the fluid path compartment in a sterile condition, wherein the cartridge is arranged in the cartridge holder of the fluid path unit such that the septum is aligned with the passage of the fluid path compartment and the first continuous flexible strip and the second continuous flexible strip contact each other and are sandwiched between the septum and the fluid path compartment, wherein the first continuous flexible strip has a first free end and the second continuous flexible strip has a second free end, the first and second free ends are arranged substantially parallel to one another adjacent the passage of the fluid path compartment, and wherein, by simultaneously pulling the first free end and the second free end, the first continuous flexible strip and the second continuous flexible strip are detachable from the assembly upon removal from the surface of the crimp and the surface of the fluid path compartment for establishing a sterile connection between the opposite first surface of the septum and the interior of the fluid path compartment.

2. The assembly for an injection or infusion device according to claim 1, wherein the barrel of the cartridge defines a first axis which is aligned with an axis of the spike or needle, and wherein the first free end and the second free end of the first continuous flexible strip and the second continuous flexible strip adjacent to the passage are oriented substantially perpendicular to the first axis.

3. The assembly for an injection or infusion device according to claim 1, wherein the first continuous flexible strip and the second continuous flexible strip sandwiched between the septum and the fluid path compartment are compressed against each other by a biasing element.

4. The assembly for an injection or infusion device according to claim 3, wherein the biasing element is a spring or ratchet acting on the barrel of the cartridge biasing the cartridge towards the fluid path compartment and/or is at least one resilient element positioned between the crimp of the cartridge and the fluid path compartment.

5. The assembly for an injection or infusion device according to claim 4, wherein the resilient element comprises an O-ring, elastic double sided adhesive tape or a flexible arm.

6. The assembly for an injection or infusion device according to claim 1, wherein the first continuous flexible strip and the second continuous flexible strip are made of a porous membrane, the porous membrane being permeable to sterilization gases.

7. The assembly for an injection or infusion device according to claim 6, wherein the porous membrane comprises polyethylene or polypropylene fibers.

8. The assembly for an injection or infusion device according to claim 6, wherein the sterilization gasses to which the porous membrane is permeable comprise one or more of ethylene oxide gas or hydrogen peroxide gas.

9. The assembly for an injection or infusion device according to claim 1, wherein the first area of the first continuous flexible strip is attached or attachable to an end surface of the crimp.

10. The assembly for an injection or infusion device according to claim 9, wherein the first area of the first continuous flexible strip is attached or attachable to the end surface of the crimp by one or more of heat sealing, an adhesive glue, a hot melt or using double sided adhesive tape.

11. The assembly for an injection or infusion device according to claim 1, wherein the second area of the second continuous flexible strip covering the passage is attached to the surface of the fluid path compartment by one or more of heat sealing, an adhesive glue, a hot melt or using double sided adhesive tape.

12. The assembly for an injection or infusion device according to claim 1, wherein the second area of the second continuous flexible strip is connected to the free end of the second continuous flexible strip by at least one U-shaped fold and/or the first area of the first continuous flexible strip is connected to the free end of the first continuous flexible strip by at least one U-shaped fold.

13. The assembly for an injection or infusion device according to claim 1, wherein the first free end and the second free end of the first continuous flexible strip and the second continuous flexible strip are connected to each other, or connected to a protective cap, or connected to a removable release liner protecting an adhesive layer configured for attaching the injection or infusion device to the skin of a patient.

14. A method for assembling an assembly for an injection or infusion device, comprising the steps of:
providing a cartridge comprising a sterile liquid medicament, formed as a barrel, the cartridge being closed by a septum fastened to the barrel by a crimp, a surface of the septum opposite to a surface contacting the liquid medicament being sterile and covered by a first area of a first continuous flexible strip attached to a surface of the crimp, thereby keeping the opposite surface of the septum in a sterile condition;
providing a fluid path unit comprising a cartridge holder and a fluid path compartment comprising a needle or spike in an interior of the fluid path compartment, wherein the needle or spike is configured to penetrate the septum of the cartridge through a passage defined in a surface of the fluid path compartment, wherein the passage is closed by a second continuous flexible strip that is attached to the surface of the fluid path compartment, the second continuous flexible strip having a second area covering the passage thereby keeping the interior of the fluid path compartment in a sterile condition; and
inserting the cartridge in the cartridge holder of the fluid path unit such that the septum is aligned with the passage of the fluid path compartment and that the first continuous flexible strip and the second continuous flexible strip contact each other and are sandwiched between the septum and the fluid path compartment,
wherein the first continuous flexible strip comprises a first free end and the second continuous flexible strip comprises a second free end, the first free end and the second free end arranged substantially parallel to another adjacent from the passage during insertion, and
wherein, by pulling the first and second free ends, the first and second continuous flexible strips are detachable from the assembly upon removal from the surface of the crimp and the surface of the fluid path compartment.

15. The method for assembling the assembly for an injection or infusion device according to claim 14, further comprising the step of:
removing the first continuous flexible strip and the second continuous flexible strip from the cartridge and fluid path compartment by simultaneously pulling the first free end and the second free end for establishing a sterile connection between the first surface of the septum and the interior of the fluid path compartment.

16. The method for assembling the assembly for an injection or infusion device according to claim 14, further comprising the step of:
sterilizing the cartridge comprising the sterile liquid medicament prior to inserting the cartridge into the cartridge holder.

17. The method for assembling the assembly for an injection or infusion device according to claim 14, further comprising the step of:
sterilizing the fluid path unit prior to inserting the cartridge into the cartridge holder.

18. The method for assembling the assembly for an injection or infusion device according to claim 14, wherein the cartridge is inserted into the cartridge holder in a non-sterile environment.

19. An injection or infusion device comprising an assembly which has been assembled in which:
the assembly comprises:
a cartridge comprising a sterile liquid medicament, formed as a barrel, the cartridge being closed by a septum fastened to the barrel by a crimp, wherein a surface of the septum opposite a surface contacting the liquid medicament being sterile and covered by a first area of a first continuous flexible strip attached to a surface of the crimp, thereby keeping the opposite surface of the septum in a sterile condition; and
a fluid path unit comprising a cartridge holder and a fluid path compartment comprising a needle or spike in an interior of the fluid path compartment, wherein the needle or spike is configured to penetrate the septum of the cartridge through a passage defined in a surface of the fluid path compartment, wherein the passage of the fluid path compartment is closed by a second continuous flexible strip attached to the surface of the fluid path compartment, the second continuous flexible strip comprising a second area covering the passage thereby keeping the interior of the fluid path compartment in a sterile condition, and
wherein:
the cartridge is inside in the cartridge holder of the fluid path unit such that the septum of the cartridge is aligned with the passage of the fluid path compartment and the first continuous flexible strip and the second continuous flexible strip contact each other and are sandwiched between the septum and the fluid path compartment,
wherein the first continuous flexible strip comprises a first free end and the second continuous flexible strip comprises a second free end, the first free end and the second free end arranged substantially parallel to another adjacent from the passage, and
wherein, by pulling the first free end and the second free end, the first continuous flexible strip and the second continuous flexible strip are detachable from the assembly upon removal from the surface of the crimp and the surface of the fluid path compartment for establishing a sterile connection between the first surface of the septum and the interior of the fluid path compartment.

20. The assembly for an injection or infusion device assembled according to claim 19, wherein the first continuous flexible strip and the second continuous flexible strip are sandwiched between the septum and the fluid path compartment and are compressed against each other by a biasing element.

* * * * *